United States Patent
Pandya

(10) Patent No.: US 10,799,301 B2
(45) Date of Patent: *Oct. 13, 2020

(54) SYSTEM AND TECHNIQUE FOR ACCESSING EXTRA ARTICULAR LESIONS OR ABNORMALITIES OR INTRA OSSEOUS LESIONS OR BONE MARROW LESIONS

(71) Applicant: Rajiv D. Pandya, Atlanta, GA (US)

(72) Inventor: Rajiv D. Pandya, Atlanta, GA (US)

(\*) Notice: Subject to any disclaimer, the term of this patent is extended or adjusted under 35 U.S.C. 154(b) by 0 days.

This patent is subject to a terminal disclaimer.

(21) Appl. No.: 16/588,548

(22) Filed: Sep. 30, 2019

(65) Prior Publication Data

US 2020/0022759 A1    Jan. 23, 2020

Related U.S. Application Data

(60) Continuation of application No. 15/889,883, filed on Feb. 6, 2018, now Pat. No. 10,441,368, which is a (Continued)

(51) Int. Cl.
*A61B 17/17* (2006.01)
*A61B 34/20* (2016.01)
(Continued)

(52) U.S. Cl.
CPC .......... *A61B 34/20* (2016.02); *A61B 17/1764* (2013.01); *A61B 17/34* (2013.01);
(Continued)

(58) Field of Classification Search
CPC ............ A61B 17/1675; A61B 17/1703; A61B 17/1714; A61B 17/1717; A61B 17/1725;
(Continued)

(56) References Cited

U.S. PATENT DOCUMENTS

| 852,394 A | 4/1907 | Moses |
|---|---|---|
| 4,257,411 A | 3/1981 | Cho |

(Continued)

FOREIGN PATENT DOCUMENTS

| GB | 2230453 | 10/1990 |
|---|---|---|
| WO | 2009107121 | 9/2009 |

OTHER PUBLICATIONS

Rotator Cuff Tears and Treatment Options, Article 2007, pp. 1-9 American Academy of Orthopaedic Surgeons, Rosemont IL, Rotator Cuff Tear, 2008, pp. 1-3 ehealth MD.

*Primary Examiner* — Anu Ramana
(74) *Attorney, Agent, or Firm* — IVC Patent Agency; David O. Simmons

(57) ABSTRACT

A technique for accessing extra articular lesions or abnormalities or intra osseous lesions or abnormalities or bone marrow lesions or all has the step of positioning the localizing pinning member onto cartilage or subchondral bone to define a virtual pathway through the cartilage or subchondral bone towards or into or through the lesion or abnormality or a desired target to create the virtual pathway utilizing an intra articular localizing pinning member to determine a location of the lesion or abnormality wherein the utilization of the localizing pinning member includes the step to locate or stabilize or both and thereafter using the virtual pathway to create an entry access.

6 Claims, 28 Drawing Sheets

Related U.S. Application Data division of application No. 15/265,178, filed on Sep. 14, 2016, now Pat. No. 9,925,010, which is a continuation-in-part of application No. 15/080,980, filed on Mar. 25, 2016, now Pat. No. 10,064,633, which is a continuation of application No. 15/080,947, filed on Mar. 25, 2016, now Pat. No. 10,064,632.

(60) Provisional application No. 62/297,478, filed on Feb. 19, 2016.

(51) Int. Cl.
  *A61B 17/34* (2006.01)
  *A61B 90/11* (2016.01)
  *A61B 17/56* (2006.01)
  *A61B 34/10* (2016.01)
  *A61B 17/88* (2006.01)

(52) U.S. Cl.
  CPC .......... *A61B 17/3472* (2013.01); *A61B 90/11* (2016.02); *A61B 17/8805* (2013.01); *A61B 2017/3405* (2013.01); *A61B 2017/564* (2013.01); *A61B 2034/107* (2016.02); *A61B 2034/2046* (2016.02)

(58) Field of Classification Search
  CPC ............ A61B 17/1764; A61B 17/1739; A61B 17/1767
  See application file for complete search history.

(56) References Cited

U.S. PATENT DOCUMENTS

| | | | |
|---|---|---|---|
| 4,672,957 A | 6/1987 | Hourahane | |
| 4,722,331 A | 2/1988 | Fox | |
| 4,739,751 A | 4/1988 | Sapega et al. | |
| 4,781,182 A | 11/1988 | Purnell et al. | |
| 4,920,958 A | 5/1990 | Walt et al. | |
| 5,112,337 A | 5/1992 | Paulos et al. | |
| 5,163,940 A | 11/1992 | Bourque | |
| 5,330,468 A | 7/1994 | Burkhart | |
| 5,556,428 A | 9/1996 | Shah | |
| 5,562,669 A | 10/1996 | Mcguire | |
| 5,669,917 A | 9/1997 | Sauer et al. | |
| 5,671,695 A | 9/1997 | Schroeder | |
| 5,681,333 A | 10/1997 | Burkhart et al. | |
| 5,766,179 A | 9/1998 | Faccioli et al. | |
| 5,895,425 A | 4/1999 | Grafton et al. | |
| 6,120,511 A | 9/2000 | Chan | |
| 6,132,433 A | 10/2000 | Whelan | |
| 6,306,138 B1 | 10/2001 | Clark et al. | |
| 6,325,804 B1 | 12/2001 | Wenstrom et al. | |
| 6,517,546 B2 | 2/2003 | Whittaker et al. | |
| 6,537,319 B2 | 3/2003 | Whelan | |
| 6,610,064 B1 | 8/2003 | Goble et al. | |
| 6,623,524 B2 | 9/2003 | Schmieding | |
| 6,716,217 B2 | 4/2004 | Mckeman et al. | |
| 6,926,720 B2 | 8/2005 | Casetnada | |
| 7,025,786 B2 | 4/2006 | Goble et al. | |
| 7,032,599 B2 | 4/2006 | May et al. | |
| 7,056,340 B2 | 6/2006 | McKeman et al. | |
| 7,175,632 B2 | 2/2007 | Singhatat et al. | |
| 7,201,756 B2 | 4/2007 | Ross | |
| 7,270,666 B2 | 9/2007 | Lomardo et al. | |
| 7,338,492 B2 | 3/2008 | Singhatat et al. | |
| 7,458,975 B2 | 12/2008 | May et al. | |
| 7,491,206 B2 | 2/2009 | Whittaker et al. | |
| 7,569,059 B2 | 8/2009 | Cerundolo | |
| 7,594,922 B1 | 9/2009 | Goble et al. | |
| 7,594,930 B2 | 9/2009 | Warlick et al. | |
| 7,674,290 B2 | 3/2010 | McKeman et al. | |
| 7,678,138 B2 | 3/2010 | Fitts et al. | |
| 7,713,300 B2 | 5/2010 | Meridew et al. | |
| 7,766,964 B2 | 8/2010 | Stone et al. | |
| 7,955,341 B2 | 6/2011 | Cerundolo | |
| 7,998,203 B2 | 8/2011 | Blum | |
| 8,088,128 B2 | 1/2012 | May et al. | |
| 8,221,454 B2 | 7/2012 | Schaffhausen | |
| 8,251,998 B2 | 8/2012 | Hoeppner et al. | |
| 8,292,921 B2 | 10/2012 | Stone et al. | |
| 8,323,291 B2 | 12/2012 | Dienst et al. | |
| 8,382,835 B2 | 2/2013 | Meridew et al. | |
| 8,435,292 B2 | 5/2013 | Whittaker | |
| 8,500,740 B2 | 8/2013 | Bojarski et al. | |
| 8,512,405 B2 | 8/2013 | Baird | |
| 8,551,123 B2 | 10/2013 | Pandya | |
| 8,579,974 B2 | 11/2013 | Pandya | |
| 8,617,166 B2 | 12/2013 | Hanson et al. | |
| 8,617,176 B2 | 12/2013 | Lizardi et al. | |
| 8,821,504 B2 | 9/2014 | Sharkey et al. | |
| 8,864,768 B2 | 10/2014 | Hanson et al. | |
| 8,906,032 B2 | 12/2014 | Hansen et al. | |
| 8,951,261 B2 | 2/2015 | Sharkey et al. | |
| 9,033,987 B2 | 5/2015 | Hanson et al. | |
| 9,119,721 B2 | 9/2015 | Sharkey et al. | |
| 9,138,187 B2 | 9/2015 | Sharkey | |
| 9,259,257 B2 | 2/2016 | Bagga et al. | |
| 9,271,835 B2 | 5/2016 | Bagga et al. | |
| 9,351,746 B2 | 5/2016 | Hanson et al. | |
| 9,351,835 B2 | 5/2016 | Sharkey et al. | |
| 9,386,996 B2 | 7/2016 | Hanson et al. | |
| 2001/0053934 A1 | 12/2001 | Schmieding | |
| 2003/0065391 A1 | 4/2003 | Re et al. | |
| 2003/0167090 A1 | 9/2003 | Chervitz et al. | |
| 2003/0176919 A1 | 9/2003 | Schmieding | |
| 2004/0059415 A1 | 3/2004 | Schmieding | |
| 2004/0087978 A1 | 5/2004 | Velez et al. | |
| 2004/0194789 A1 | 10/2004 | Whelan | |
| 2004/0225358 A1 | 11/2004 | Goble et al. | |
| 2005/0065533 A1 | 3/2005 | Magen et al. | |
| 2005/0149187 A1 | 7/2005 | Clark et al. | |
| 2006/0149259 A1 | 7/2006 | May et al. | |
| 2006/0235516 A1 | 10/2006 | Cavazzoni | |
| 2006/0241657 A1 | 10/2006 | Cerundolo | |
| 2006/0265063 A1 | 11/2006 | Goble et al. | |
| 2007/0162123 A1 | 7/2007 | Whittaker et al. | |
| 2007/0208356 A1 | 9/2007 | Cerundolo | |
| 2007/0233151 A1 | 10/2007 | Chudik | |
| 2008/0058929 A1 | 3/2008 | Whelan | |
| 2008/0154271 A1 | 6/2008 | Berberich et al. | |
| 2009/0069846 A1 | 3/2009 | Bull et al. | |
| 2009/0187244 A1 | 7/2009 | Dross | |
| 2010/0312341 A1 | 12/2010 | Kaiser et al. | |
| 2010/0324676 A1 | 12/2010 | Albertorio et al. | |
| 2011/0153018 A1 | 6/2011 | Walters et al. | |
| 2012/0095556 A1 | 4/2012 | Re et al. | |
| 2013/0023988 A1 | 1/2013 | Sinnott et al. | |
| 2013/0090731 A1 | 4/2013 | Walker | |
| 2013/0096677 A1 | 4/2013 | Myers et al. | |
| 2015/0150616 A1 | 6/2015 | Sharkey et al. | |

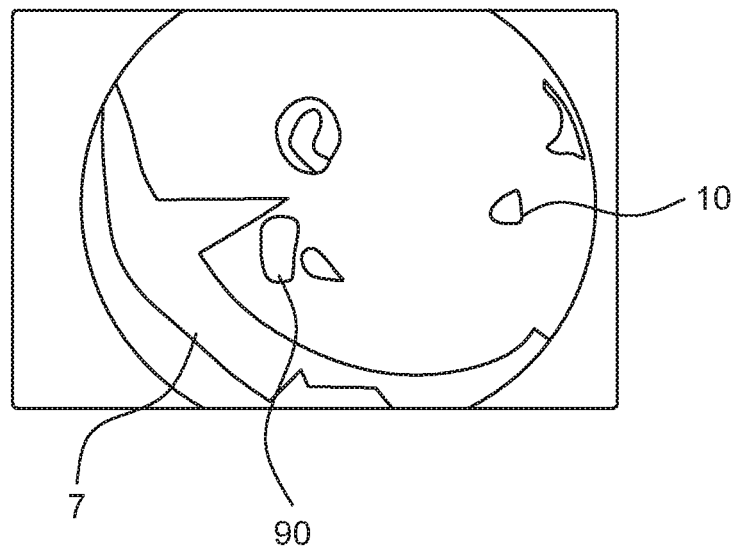
FIG. 8
PRIOR ART
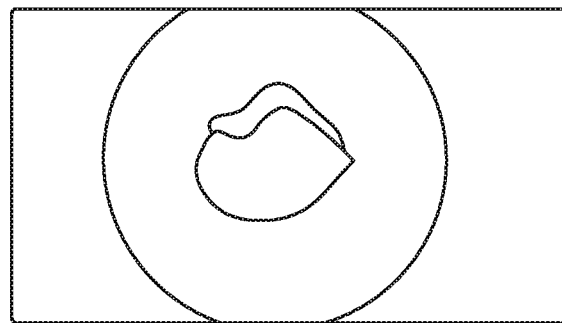
FIG. 9
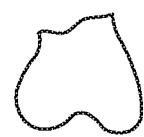  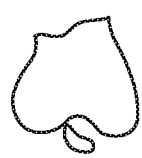
FIG. 9A     FIG. 9B     FIG. 9C

SYSTEM AND TECHNIQUE FOR ACCESSING EXTRA ARTICULAR LESIONS OR ABNORMALITIES OR INTRA OSSEOUS LESIONS OR BONE MARROW LESIONS

RELATED APPLICATIONS

This application is a continuation of co-pending U.S. application Ser. No. 15/889,883 filed on Feb. 6, 2018 entitled, "System And Technique For Accessing Extra Articular Lesions Or Abnormalities Or Intra Osseous Lesions Or Bone Marrow Lesions", which is a division of co-pending U.S. application Ser. No. 15/265,178 filed on Sep. 14, 2016 entitled, "System And Technique For Accessing Extra Articular Lesions Or Abnormalities Or Intra Osseous Lesions Or Bone Marrow Lesions", which is a continuation of U.S. application Ser. No. 15/080,947 filed on Mar. 25, 2016 entitled, "System And Technique For Accessing Extra Articular Lesions Or Abnormalities Or Intra Osseous Lesions Or Bone Marrow Lesions" which is a continuation-in-part of co-pending U.S. application Ser. No. 15/080,980 filed on Mar. 25, 2016 entitled, "System And Technique For Accessing Extra Articular Lesions Or Abnormalities Or Intra Osseous Lesions Or Bone Marrow Lesions", which claims priority from provisional application 62/297,478 filed on Feb. 19, 2016 entitled, "System And Technique For Accessing Extra Articular Lesions Or Abnormalities Or Intra Osseous Lesions Or Bone Marrow Lesions".

FIELD OF THE INVENTION

The present invention relates to the field of addressing lesions of bone marrow. A system and technique for accessing extra articular lesions or abnormalities or intra osseous lesions or bone marrow lesions is taught.

BACKGROUND OF THE INVENTION

Surgical procedures to repair bone defects such as lesions or abnormalities typically involve scooping out the damaged tissue material. One such procedure is called curettage. In these procedures, the bone is removed or opened to provide access to the lesion or cancerous tumor. This effectively weakens the bone structure because not only has the damaged tissue been removed, but also some of the load bearing solid bone structure. This is particularly problematic in the spine, the knees and the shoulder and articulating joints.

Ideally the surgeon would prefer to attack the problematic tissue without damaging the surrounding load bearing bone tissue. This is particularly difficult, however, because the damaged tissue material to be removed is hidden behind the joint. The current state of the art does not allow for accessing as well as addressing lesions of bone distant to the entry point of the localizing site.

The presently available systems and techniques do not adequately address this concern. The present invention described below provides an improved technique to remove the lesion, tumor or other abnormality without damaging the outer joint bone structure, and the surrounding cartilage, and soft tissue. This enables the healing and functionality of the repaired joint to be faster and far less painful.

Definitions

Bone cement: The bone cement PMMA (polymethylmethyacrylate) starts out as a liquid and hardens over time. It can be put into a hole in the bone in liquid form. As PMMA hardens, it gives off a lot of heat. The heat helps kill any remaining tumor cells. This allows PMMA to be used without cryosurgery for some types of bone tumors.

Bone Lesions: Various disorders can damage bones and result in bone lesions. Symptoms include bone pain or tenderness, and the injury can only be seen using special imaging tests. Bone lesions are abnormal areas of bone typically identified using an X-ray or MRI. Lucent bone lesions are caused by rapidly progressing bone injuries. Sclerotic lesions are bone injuries that develop more slowly, which allows the bone to attempt to wall off the damaged bone tissue. Bone lesions typically have cancerous and non-cancerous causes.

Bone Marrow Lesions: (BMLs), common osteoarthritis-related magnetic resonance imaging findings, are associated with osteoarthritis progression and pain.

Curettage: In this procedure, the doctor scoops out the tumor from the bone without removing a section of the bone. This leaves a hole in the bone. In some cases, after most of the tumor has been removed, the surgeon will treat the nearby bone tissue to kill any remaining tumor cells. This can be done with cryosurgery or by using bone cement.

Cryosurgery: For this treatment, liquid nitrogen is poured into the hole that is left in the bone after the tumor was removed. This extremely cold material kills tumor cells by freezing them. This treatment is also called cryotherapy. After cryosurgery, the hole in the bone can be filled by bone grafts or by bone cement.

Osteoarthritis: is the most common form of arthritis, affecting millions of people worldwide. It occurs when the protective cartilage on the ends of your bones wears down over time.

Osteochondritis dissecans: (OCD or OD) is a joint disorder in which cracks form in the articular cartilage and the underlying subchondral bone. OCD usually causes pain and swelling of the affected joint which catches and locks during movement. OCD is caused by blood deprivation in the subchondral bone. This loss of blood flow causes the subchondral bone to die in a process called avascular necrosis. The bone is then reabsorbed by the body, leaving the articular cartilage it supported prone to damage. The result is fragmentation (dissection) of both cartilage and bone, and the free movement of these bone and cartilage fragments within the joint space, causing pain and further damage. OCD can be difficult to diagnose because these symptoms are found with other diseases. However, the disease can be confirmed by X-rays, computed tomography (CT) or magnetic resonance imaging (MRI) scans.

Subchondral bone: bone located beneath or below the cartilage.

SUMMARY OF THE INVENTION

A system for accessing extra articular lesions or abnormalities or intra osseous lesions or abnormalities or bone marrow lesions or all has an intra articular localizing pinning member to determine a location of the lesion or abnormality. The utilization of the localizing pinning member includes positioning the localizing pinning member onto cartilage or subchondral bone to define a virtual pathway extending through the lesion or abnormality to locate or stabilize or both prior to creating a first entry access. The localizing pinning member never enters the bony lesion or abnormality but creates the virtual pathway penetrating at least into or through the lesion or abnormality when set by holding the localizing pinning member positioned establishing a desired depth of a target location along the virtual pathway. The system further has a guide component attachable to an exposed portion of the localizing pinning member at a predetermined position on a shank of the localizing pinning member. Manipulating the guide component about the localizing pinning member establishes the desired target location for the creation of the first entry access based on the relevant anatomy.

The guide component is adjustably movable to be set or fixed at the desired first entry access point. The first entry access point can be moved so a track extending from the first entry access point is adjustably aligned to intersect the virtual pathway at the desired target location or adjusted therefrom by a fixed distance on the virtual pathway.

The system further has an adjustably movable guide having an opening for passing a drill, a pin or a punch, the opening being translatable about the guide component to form the first entry access to a desired depth within or in the proximity of the lesion or abnormality.

The guide component has a first arm for attachment to the localizing pinning member and a second arm for guiding a drill, a punch or a pin, the second arm being movably attached to the first arm. The second arm has an arcuate portion extending to a straight portion, the second arm being coupled to and selectively movable relative to the first arm along the straight portion of the second arm. The straight portion of the second arm has a calibrated scale extending along at least a portion of a length of the straight portion. A movement of the second arm relative to the first arm along the straight portion of the second arm correspondingly adjusts the first entry access location.

The first arm has a coupling end for attachment to the straight portion of the second arm. The straight portion of the second arm and the coupling end of the first arm includes a distance adjustment mechanism to linearly move the second arm relative to the first arm. The distance adjustment mechanism can be one of a screw, a gear, a ratchet, a wheel, a dial or a clip mechanism that moves the second arm to a desired adjusted distance along the virtual pathway relative to an intersection point of a track of a drill, punch or pin and the virtual pathway.

The first arm can be made disposable or non-disposable. The first arm is preferably detachable for interchangeable arms having different tips, the tip being fixed, movable, annular, open, having a cross hair for targeting or having points, flats or a guide sleeve.

The first arm is detachably coupled to the second arm. The second arm can be made of metal.

The system provides for a technique for accessing extra articular lesions or abnormalities or intra osseous lesions or abnormalities or bone marrow lesions or all. The technique has an intra articular localizing pinning member to determine a location of the lesion or abnormality, positioning the localizing pinning member onto cartilage or subchondral bone to define a virtual pathway through the cartilage or subchondral bone towards or into or through the lesion or abnormality or a desired target to create the virtual pathway wherein the surgeon selects a desired depth along the virtual pathway to establish the desired target securing an adjustable guide component to an exposed portion of the localizing pinning member at an appropriate position on a shank of the localizing pinning member manipulating the guide component while stabilizing the localizing pinning member to establish a desired location for an entry access based on the relevant anatomy, the adjustable guide component is set or fixed at the entry access point, the adjustable guide component being movably adjustable to set or fix a track of the entry access to intersect the virtual pathway at a preselected position. The technique further has a step of utilizing the fixed or set adjustable guide component to pass a drill, a pin or a punch at the entry access to a desired depth within or in the proximity of the lesion or abnormality, wherein the entry access alignment is directed by the position of the localizing pinning member and the adjustable guide component, wherein straight lines, one line extending along a track of the localizing pinning member defining the virtual pathway and one line extending along a track of the drill, pin or punch forming the entry access intersect.

The one line extending along the track of the drill pin or punch can be adjustable parallel to the line by a predetermined distance (d) by the adjustable guide component to the track of the drill intersects the virtual pathway at a location offset by the distance (d). The virtual pathway extends coincident with the localized pinning member through the desired target and the entry access has an end at least in proximity to, in or through the lesion or abnormality wherein the desired target is located short of the one line extending along the track of the first access entry, beyond or an intersection.

The technique further has the step of utilizing the access entry to do one or more of the following steps: a) delivering a substance or material to the proximity or location of the lesion or abnormality; b) modifying the lesion or abnormality; and c) introducing devices to modify or visualize the lesion or abnormality. The technique of claim 23 further comprises the step of securing a guide component to an exposed portion of the localizing pinning member at a predetermined position on a shank of the localizing pinning member manipulating the guide component about the localizing pinning member to establish a desired location for the creation of one or more entry access points based on the relevant anatomy, and placing one or more pins or anchors through the cartilage and subchondral bone or through the subchondral bone, and filling the lesion cavity with bone cement or other fixing material passed through one of said entry access to structurally support the pins to repair the bone.

The lesion or abnormality is a tumor or an infection in affected tissue. The surgeon treating a tumor or infection removes some or all of the affected tissue and further introduces stabilizing material. The stabilizing material can include bone substitutes, bone cements, antibiotics, chemotherapy medication, stem cells, or any combinations thereof.

BRIEF DESCRIPTION OF THE DRAWINGS

The invention will be described by way of example and with reference to the accompanying drawings in which:

FIG. 8 is an example of a prior art lesion fixation.

FIG. 9 shows a bone lesion.

FIGS. 9A, 9B and 9C show diagrammatically how the lesion can be separated exposing the bone marrow.

DETAILED DESCRIPTION OF THE INVENTION

Figure 1:
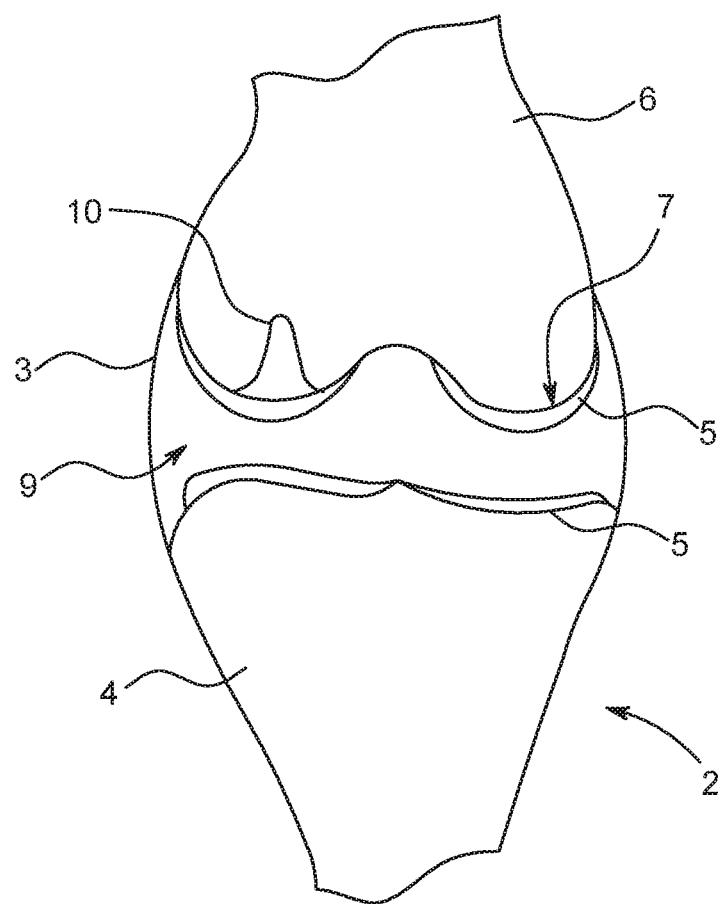
FIG. 1 shows a plan or frontal view of a relatively normal joint with the bone marrow lesion from osteochondritis dissecans with the femur above and the tibia below.

With reference to FIGS. 1-7, a first embodiment of the present invention is illustrated. The first embodiment of the present invention provides for a pinning member access 11, which is the first entry access, to be created through the cartilage 5 and subchondral bone 7 using a guide component 21 which further enables a localizing pinning member 30 to penetrate into the first entry access 11 and by utilizing the guide component 21 allows for a precise location for a second entry access 12 location to be created. The guide component 21 consists of first arm 22 and second arm 24 including the straight portion 24A.

Figure 10:
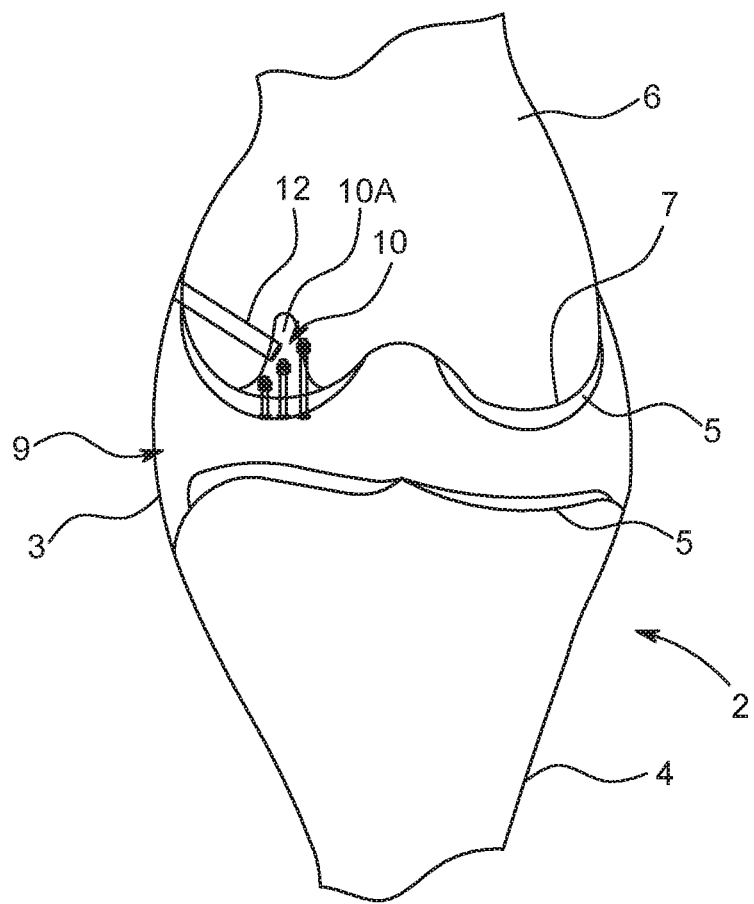
FIG. 10 is a joint showing fixation anchors or pins pre-set through the subchondral bone and cartilage with the second access extending toward the end of the pins.
Figure 11:
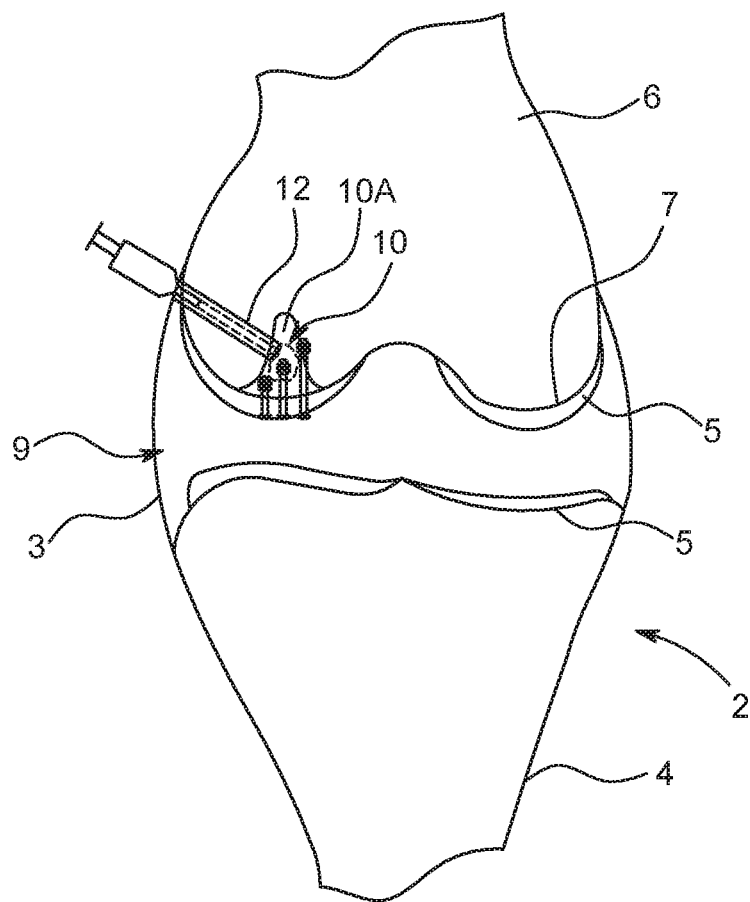
FIG. 11 shows how a bone cement can be injected with a filled syringe into the lesion or abnormality cavity to encapsulate the pins or bone anchors.
Figure 12:
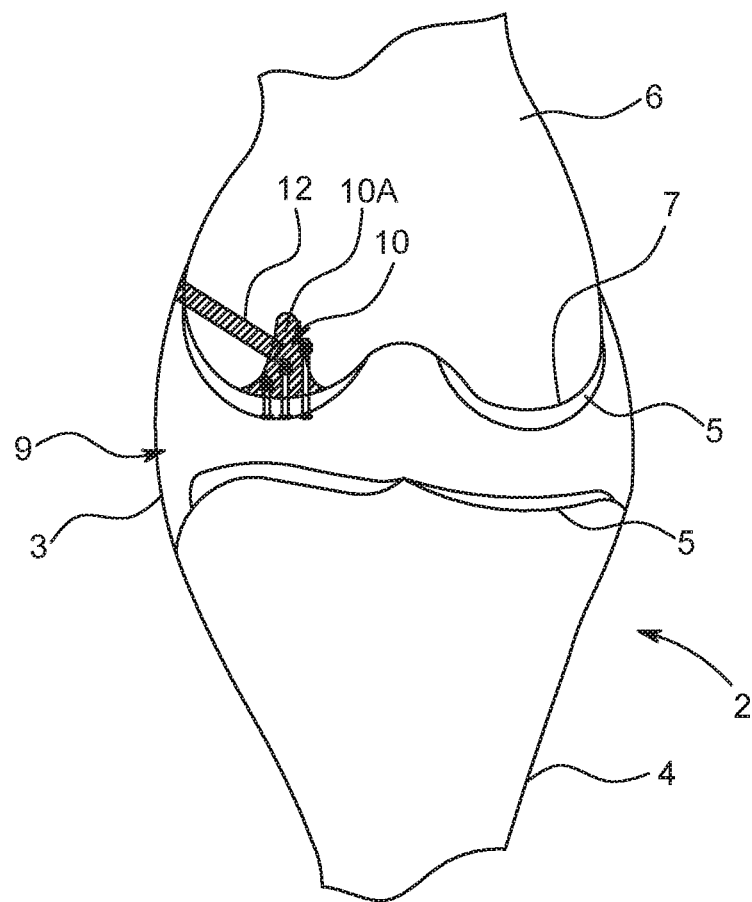
FIG. 12 shows the repair structurally cemented and fully supported lesion or abnormality repair.
Figure 13:
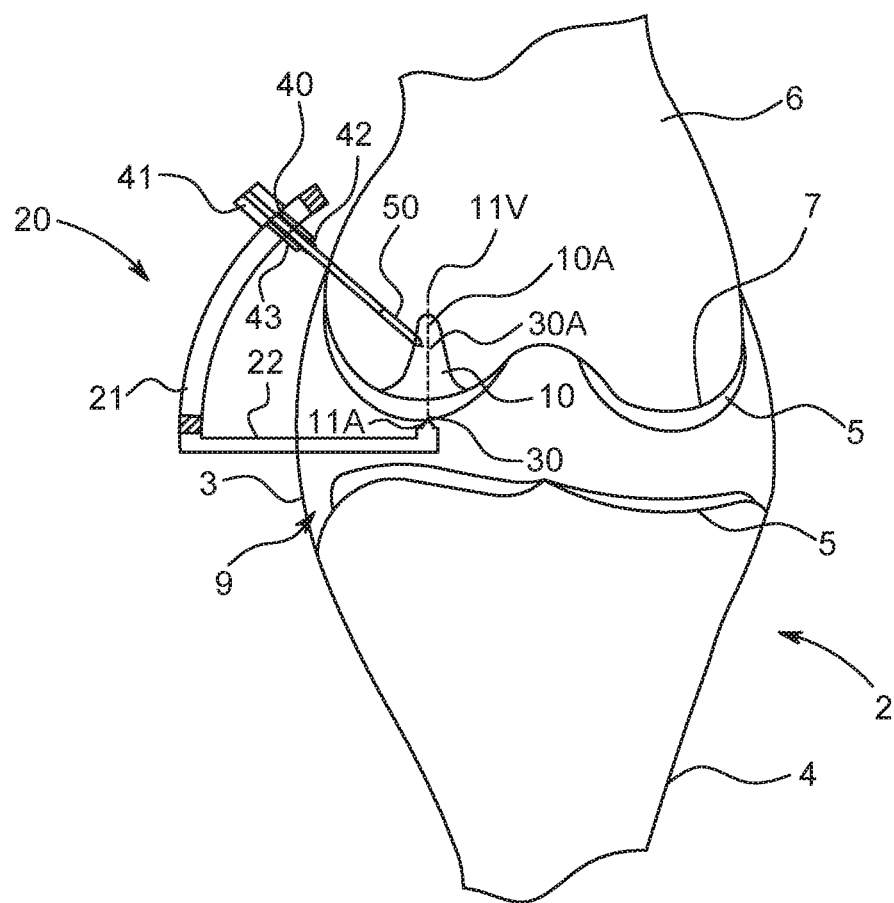
FIG. 13 shows a second embodiment of the invention wherein a virtual pathway is used when positioning the localizing pinning member which does not penetrate through subchondral bone or the cartilage as illustrated, but rather is located on the cartilage.

With reference to FIGS. 10-12, pins or anchoring devices 90 can be inserted through cartilage 5 and subchondral bone 7 into a lesion 10 or abnormality and the creation of a second entry access 12 location provides a means through which the pins or anchors 90 can be structurally supported by the addition of bone cement 62. A syringe 60 can be placed into the second entry access 12 through which the bone cement 62 or other fixing agents can be syringed through the second entry access portal 12 into the lesion 10 to encapsulate the bone screw 90, as shown in FIG. 11. In FIG. 12, the residual cement 62 that is packed into the cavity where the abnormality or lesion was and the second entry access is filled as illustrated sealing the opening wherein the anchors 90 are firmly secured. This structurally supporting cementing of the pins or anchors 90 works equally well with the second embodiment of the present invention wherein the entry access 12 is used to fill the lesion cavity 10, 10A and seal the angled tunnel or track entry access 12 to support the pins or anchors 90.

With reference to FIGS. 13-18, the second embodiment of the invention is illustrated. This second embodiment is very similar to the first embodiment. However, the localizing pinning member 30 creates a virtual pathway 11V through the cartilage 5 and subchondral bone 7 without requiring a pinning member 30 entry access 11 whereby an entry access 12 can be created that intersects a line $L_1$ projected along the virtual pathway 11V from an end of the localizing pinning member 30 in such a way that the entry access $L_2$ when projected along a track will intersect at a target location along the virtual pathway 11V. In this embodiment, as will be discussed later, the subchondral bone and cartilage need not be penetrated and no pinning member entry access opening is created. However, the virtual pathway 11V is created projecting to a lesion allowing the surgeon to precisely direct and create one or more than one entry access portals or openings 12, 14 using the guide component 21 of the present invention.

The present invention addresses lesions 10 of bone, as shown in FIG. 1, which may or may not be visualized arthroscopically. This could be in situations where the patient has intact articular cartilage 5, such as the situation with osteochondritis dissecans. The surgeon can tell where the lesion 10 is by probing. There can be situations dealing with osteoarthritis or other lesions of the bone marrow where the subchondral bone 7 is intact. In either case, the surgeon wants to be able to locate where the lesion 10 of the bone is that can't be visualized, it is essentially extra articular, it is within the bone. This could be termed a bone marrow lesion, but in this technique, the surgeon uses intra articular techniques to access the lesion.

The current art on this is very limited because generally it would be utilizing fluoroscopy or other means to vaguely localize where that lesion might be. Sometimes the lesion can't even be seen on fluoro. One may argue that a pin can be placed in through it, but there are no localizing techniques other than fluoro and imaging which have significant limitations.

Figure 2:
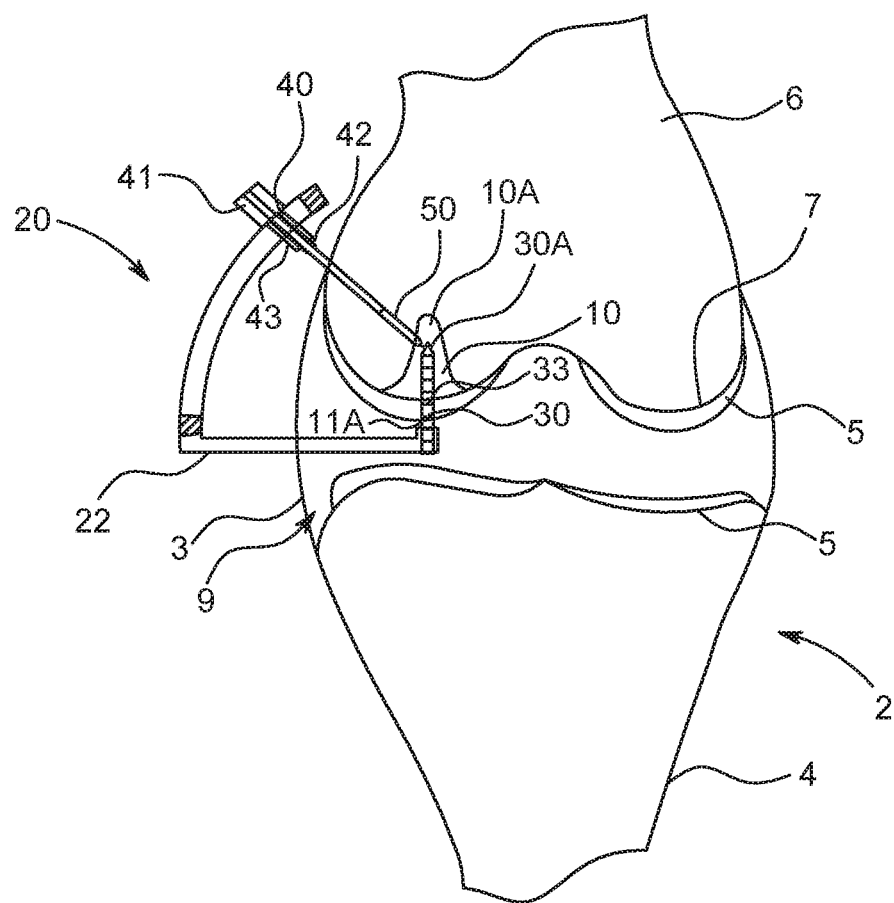
FIG. 2 shows the normal joint of FIG. 1 with the system of the present invention.
Figure 3:
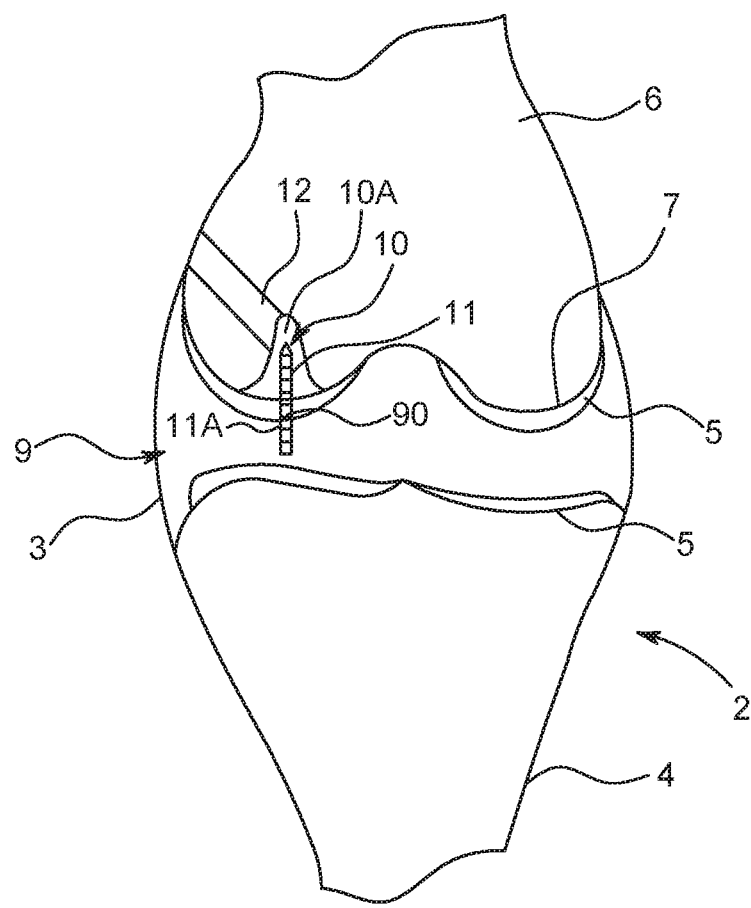
FIG. 3 demonstrates the normal joint with the first entry access and second entry access formed and the system device removed.
Figure 3A:
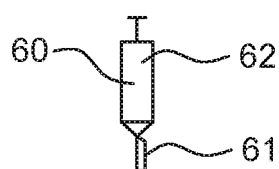
FIG. 3A is a plan view of an exemplary syringe filled with a bone putty or similar material for injection through the second entry access.
Figure 3B:
FIG. 3B is an exemplary camera or imaging scoping device for visualizing the lesion through the second entry access.

In the first embodiment of the present invention, as shown in FIG. 2, the provided device or system 20 of the present invention allows the surgeon to actually put a pinning member 30 into the lesion 10 through articular cartilage 5, or in a situation of the osteochondritis dissecans lesion, the surgeon can place the pinning member 30 through the subchondral bone 7 to address a bone marrow lesion 10. The surgeon applies a guide component 21 to that localizing pinning member 30. The guide component 21 has a movable guide 40 forming a system that allows for extra articular access to the end or point of the localizing pinning member 30 which is something that is not visualized, but rather is something within that bone marrow lesion 10 or within the bone at a point 10A distal from the intra articular visualized entry point 11A and access to it occurs from outside the joint 2. The surgeon could actually access it from even inside the joint 2, but coming from a different point or direction. And now by accessing the lesion 10 and removing the damaged tissue, the surgeon can introduce substances into it, such as bone mineral grafting, calcium phosphate, etc. or you can even put a camera system 70, as shown in FIG. 3B, through the second entry access track or portal 12 that was created to look at or modify the lesion 10 by putting different types of reamers 80, shown in FIG. 3C, into it and selected substances using a syringe 60 filled with a material 62 such as putty or bone allograft or bone cement, as shown in FIG. 3A. Then one can, after that has been done, put fixation pins 90 additionally into it from the intra articular utilizing the initial pinning member 30 access 11, one can put pins and fixation devices 90 around it to help further fix the lesion, as shown in FIG. 3.

The limitation of the prior art techniques is that they allow for no precise localization of lesions which cannot be seen. It may be argued that when one uses the prior art guide systems, the problem is that these create straight tracks. The prior art in line devices don't create angled tunnels, this inventive technique requires an angled tunnel to be created because the surgeon wants the extra articular point of entry to be somewhere remote from the pinning member 30 entry point 11A which is the intra articular localizing point 11A. The best way to do that is to create an angled tunnel or an angled track. If using the standard prior art in-line guides, with its exit point at the intra articular point coming in from outside in, one does not create an appropriate track and can actually violate that subchondral bone and the lesion. Furthermore, this does not provide an appropriate methodology for introducing substances in a sophisticated manner or in a precise manner. The present invention is a complete and different approach to it and introduces and provides an entirely new system of devices and instruments to be used for these purposes. Limitations of the prior art as mentioned before is there are no methodologies for addressing and accessing lesions one cannot see when one wants to visualize or repair remote from the initial entry localizing point. That is a big difference.

The present invention allows for precise localization of a lesion 10 and a way to access it while minimizing load bearing bone structure damage caused by the surgical repair by essentially leveraging the inventor's angled osteal tunnel concept of creating blind tunnels. In the first embodiment, the surgeon is now able to drill a hole 11 into subchondral bone 7 of the femur 6 and from another angled entry point create an access track or portal 12 so the tip of that pinning member 30 and the drill 50 extend along intersecting lines $L_1$ and $L_2$ so that the location 10A is triangulated. This allows for precise localization of the lesion 10 and access to it.

One example where this is most useful is to access the lesion 10 from within the joint 2 such as the knee joint 2. This is called intra-articular. The surgeon can drill a pinning member 30 from within the joint 2 into the bone even going through intact cartilage if necessary. Then, from coming outside of the joint 2 with another drill 50, he or she can then articulate to a blind spot or point 10A within bone knowing it is accurate based on the precision of the guide system 20 instruments. Often times, the lesion 10 being addressed maybe a cystic lesion. The surgeon can then introduce other reamers 80 into this second access portal 12, the reamer 80 is configured to expand at tip 82 once it gets to that desired lesion spot to clean this out. The removed lesion tissue forms a cavity which can then be filled with bone grafting material substance 62 through a cannula 61 that came in from outside of the joint 2. This technique uniquely allows for blind targeting a point or location 10A within bone. The invention in an earlier angled osteal tunneling technique, was for retrieving sutures. In this technique, the surgeon is using the angled tunnels as portals 12, 14 for delivering material 62 to that spot. Additionally, he can also place a camera 72 through one of the portals 14, see FIG. 7, which will then allow for him to directly visualize what is taking place within the lesion 10 using one portal 14 for the camera 72 and another portal 12 for instruments. As shown, the camera 72 is connected by a flexible cable or tube 71 to a display monitor 78 for real time viewing.

One of the best examples of utilization of this technique is in the case of osteochondritis dissecans. This is a serious lesion in children and young adults where the cartilage 5 can be intact within the joint 2, but the bone 7 behind it essentially cystic or a vascular. The surgeon knows where the lesion 10 is from looking inside the joint 2, but he can't access the dead bone without violating the cartilage 5. Hence, with this inventive technique, he simply drills up in through the intact cartilage to help stabilize it using the pinning member 30. Then coming from outside the joint 2 he can address the diseased bone, clean it out and put material 62 using the second entry access portal 12. He can then, from inside the joint 2, further stabilize the lesion 10.

There are a number of key points the inventor would like to emphasize regarding the present invention. First, the access to a bony lesion 10 from within a joint (intra-articular) or from outside the joint (extra articular) is greatly enhanced. The ability to use the tunnel portal tracks 12, 14 either for retrieval or for delivery of materials 62 is achieved. The ability to use the tracks 12, 14 to place cameras 72 and working instruments 80 to look inside of the bony lesions 10 is accomplished. The precise targeting of bony lesions 10 blindly using a technique of triangulation with the guide system 20 instruments or devices of the present system is available.

FIG. 1 shows a relatively normal joint 2 with the bone marrow lesion 10 from osteochondritis dissecans, as shown the joint 2 has the femur 6 above and the tibia 4 below. The figure outlines the articular cartilage 5 and right behind the cartilage is subchondral bone 7. Also drawn is the capsule 3, anything outside the capsule 3 is what is called extra articular; inside the capsule 3 is called intra articular space 9. The bone marrow lesion 10 which is hidden from view because it is behind that cartilage 5. It may be behind subchondral bone 7 in a situation where you have arthritis and don't actually have that cartilage over it. The point is one can't see the lesion 10 behind what they are looking at from the scope.

FIG. 2 shows how this would be addressed. The surgeon would put a pinning member 30 through the cartilage 5 and the subchondral bone 7 or just the subchondral bone 7 if there was no cartilage 5, so it actually goes into the bone marrow lesion 10. This pinning member 30 can go into it or it can go all the way through the lesion 10. Then, utilizing the guide system 20, coming from outside in a generally extra articular approach, but it may not be if it just comes in from a different direction to form a second or even more access portals 12, 14. In any event, these second and one or more additional portals 12, 14 do not go through the articular cartilage 5. The key is that the surgeon is accessing this lesion 10 within the bone from a safe area that doesn't damage the joint 2. The access doesn't damage the other anatomical structures; that is why he has to have the variability of a range of depth and the variability of a range of angles combined with the ability to rotate the guide component 21 around the axis of the pinning member 30. One can't have a fixed point of entry because that can be dangerous. This adjustment capability allows the surgeon to access the lesion 10 from a different location, generally an extra articular location, that's what's demonstrated how the guide 20 works on this example as shown in FIG. 2.

Figure 3C:
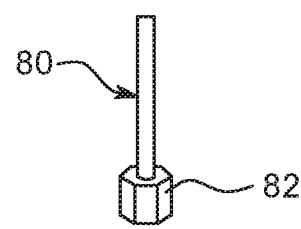
FIG. 3C is an example of an expandable reamer for cleaning the lesion material during repair through the second entry access.

FIG. 3 demonstrates what is done when you have that track formed on an angled osteal tunnel access portal 12. Once that separate track 12 is created, the surgeon can enlarge the track 12 with reamers 80, can put different types of reamers 80 in, which are small going in, then they expand once they get to the lesion 10, flip cutters, or other types that can be utilized in that situation. The surgeon can use the track or access portal 12, 14 to fill the cavity created when the lesion tissue is removed with different substances 62 including bone mineral matrices, stem cells, or can even put cameras 72 inside. As illustrated, a putty filled syringe 60, a camera system 70 or an expandable reamer 80 with tip end 82 can be used, as shown in FIGS. 3A, 3B and 3C respectively. Once filled in, these different substances can set, then the surgeon can go back into the joint 2 and can put multiple pins 90, and fixation devices 90 which can now be better fixed because there is some substance within the lesion 10 cavity which to fix them to.

Figure 4:
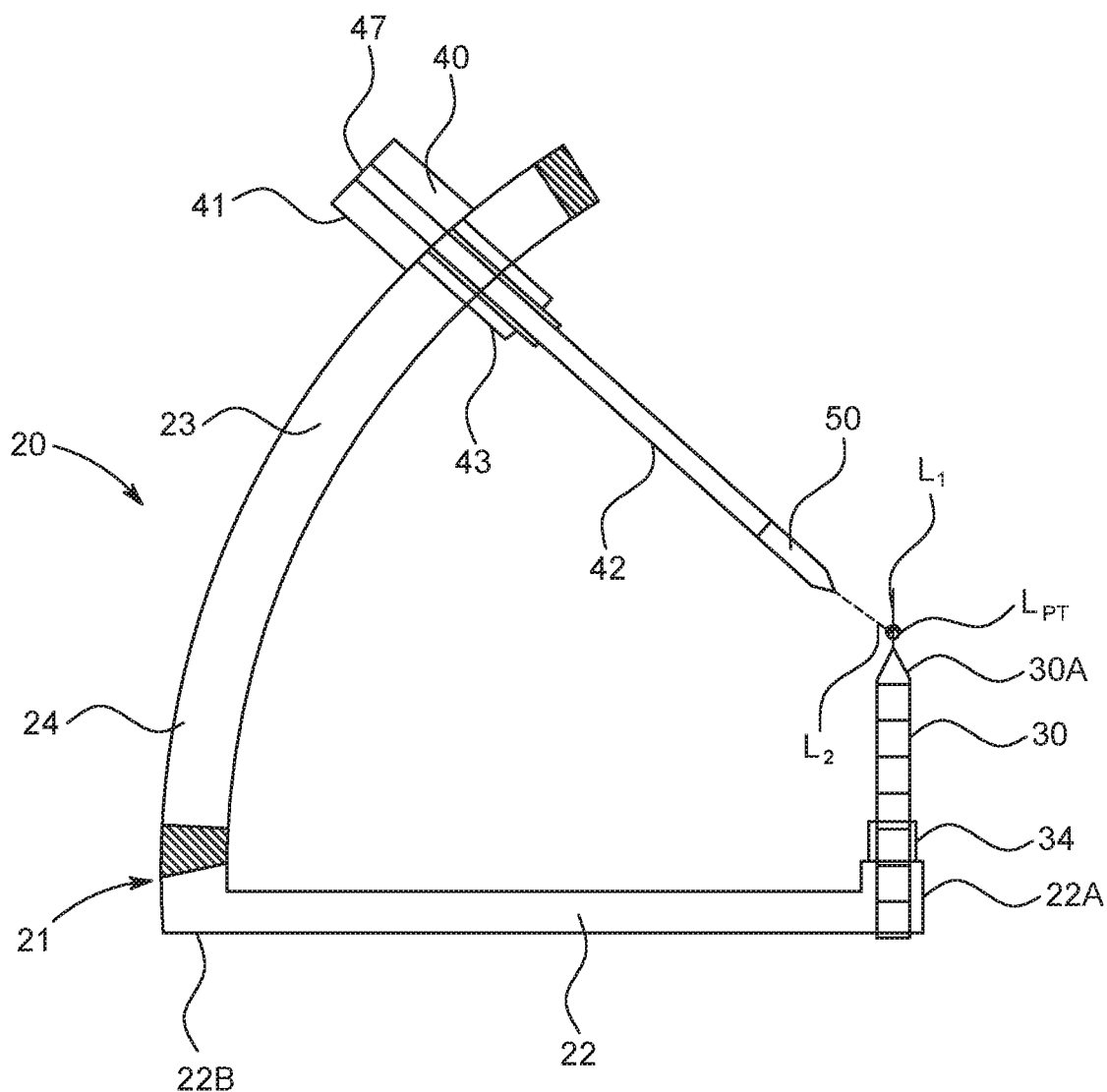
FIG. 4 demonstrates the guide system of the first embodiment of the present invention.

FIG. 4 demonstrates what the guide system 20 looks like. It demonstrates how an intra articular guide pinning member 30 is placed, how the guide component 21 then attaches to the pinning member 30 at an appropriate depth. The guide component 21 has a swinging arcuate arm 24 that comes around and allows the precise localization and alignment tip to tip even though one can't see what is essentially a blind tip 10A. This allows access for things you can't see. Again, completely eclipses any type of current prior art using poor techniques such as fluoro, etc. for visualization. With the present invention, the surgeon knows exactly where he is with precise localization for addressing the lesion in a completely different way of practicing medicine.

Figure 5:
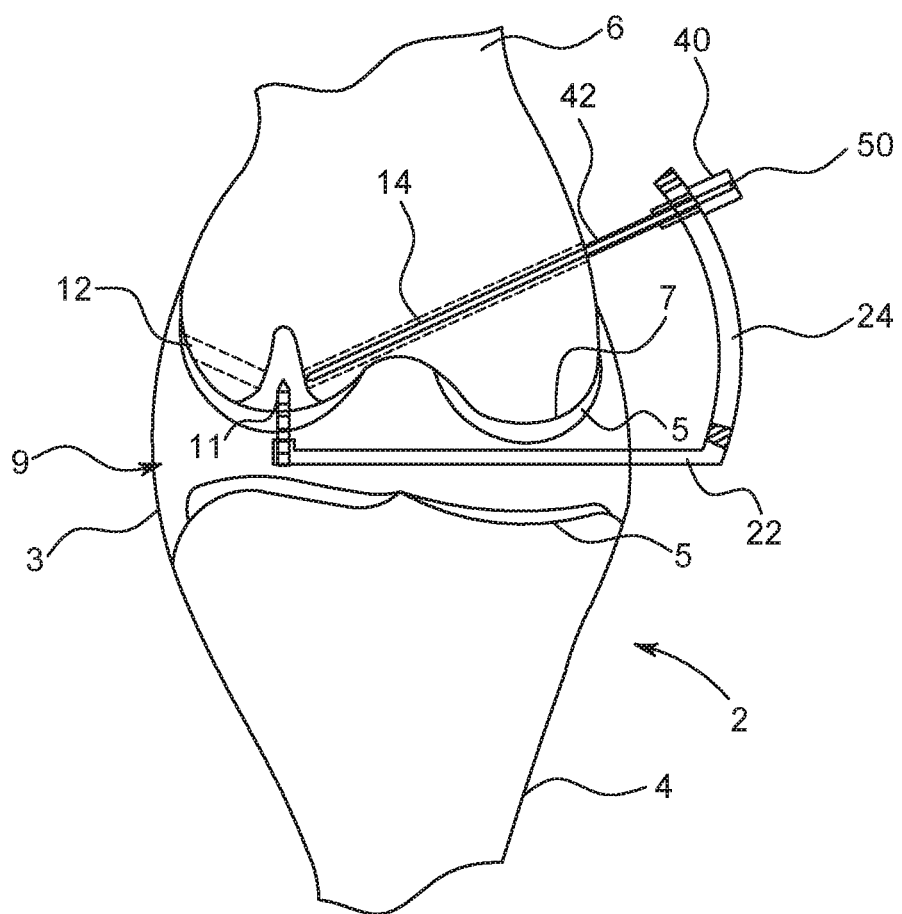
FIG. 5 is a second view of the joint of FIG. 1 showing an additional entry access with the guide system of the first embodiment in place.
Figure 6:
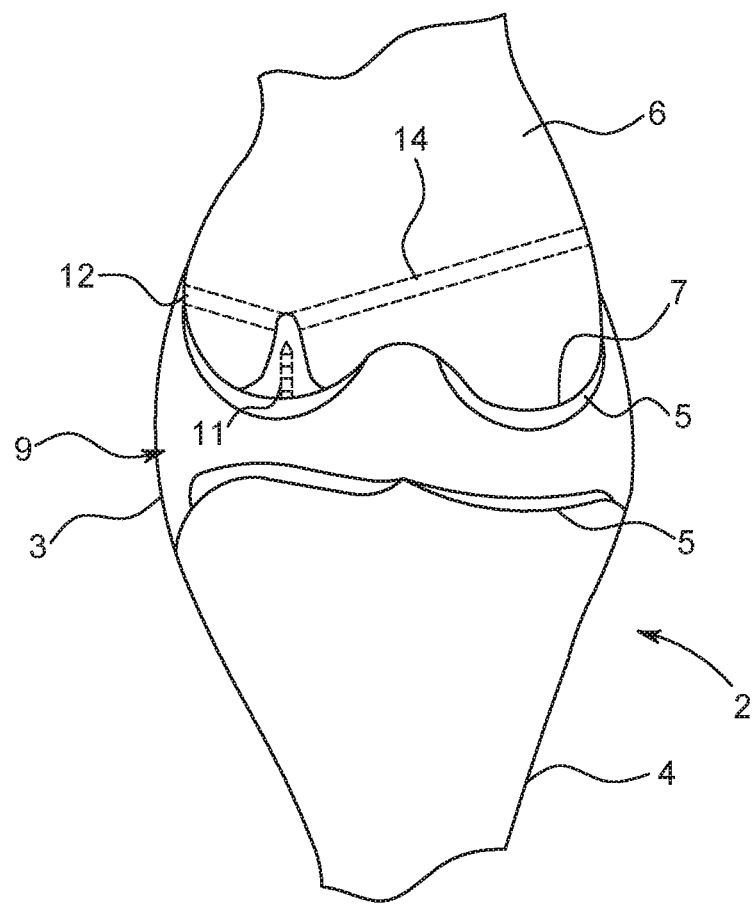
FIG. 6 shows the second view with the guide system of the first embodiment removed.
Figure 7:
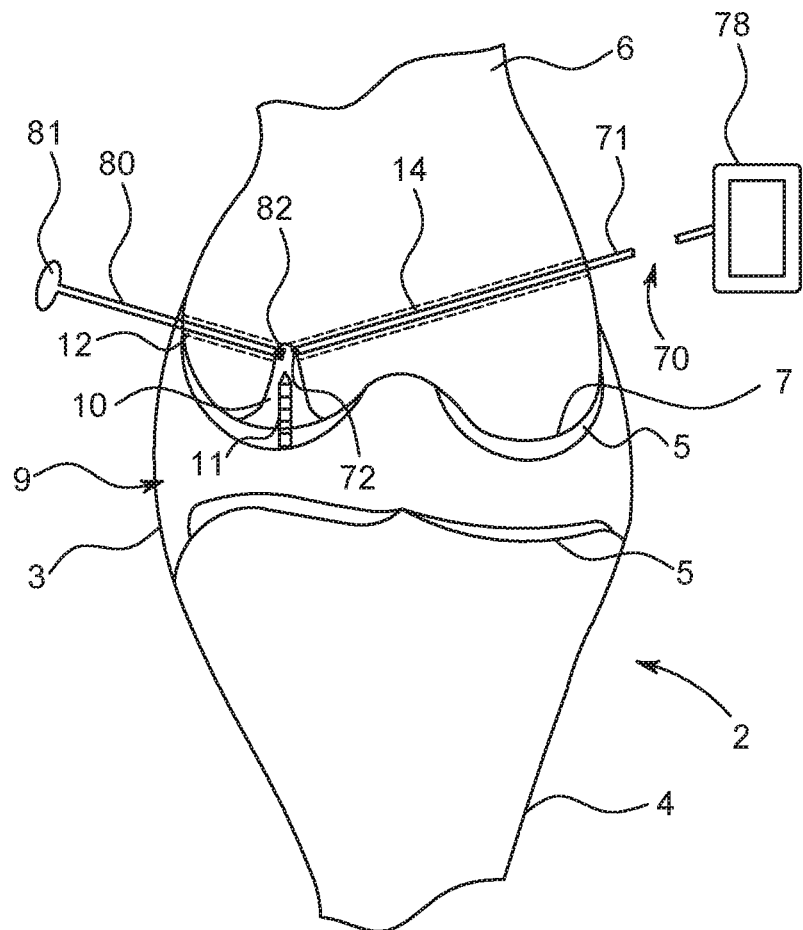
FIG. 7 shows a camera in the second entry access.

As shown in FIG. 4, the guide system 20 has a guide component 21. The guide component 21 has a straight first arm portion 22 that extends in a straight path to an end 22A for holding a pinning member 30. The end 22A is transverse to the arm portion 22. As shown, the shank of the pinning member 30 has marked gradations 33 that establish the distance to the tip or point 30A. The pinning member 30 can be a pin, a drill bit or punch, by way of example. At the end 22A, a shank tightening nut 34 or fixation device is shown that, when tightened, holds the pinning member 30 securely to the arm 22 thereby fixing the tip 30A location. At the opposite end 22B of the first or straight arm 22 is a second swing or arcuate arm 24. The second arm 24 is shown in a partial section view showing a slot 23 that allows a movable guide 40 to slide in the slot 23 over a range of angles between at least 0 and 90 degrees relative to the tip of the pinning member 30, most typically between 30 and 60 degrees. Preferably, the movable guide 40 has a cannulated shaft, sleeve or tube 42 with a tightening clamp 41 having a nut 43 that fixes the movable guide 40 onto the second arm 24 anywhere along the slotted opening or slot 23. As shown, a drill bit, a punch or a trocar 50 can be slipped through the movable guide 40 tube 42 to create the second access portal or track 12, 14. Preferably, when locating the desired location to form the second or additional access portals, the tube 42 is moved relative to the guide 21 to set the tube solidly against the tissue then the components are tightened to fix the angle and the sleeve length. Then the drill 50 can be inserted to create the second or more access tracks or portals 12, 14. The shape of the guide component 21 allows the system 20 to be pinned at one location and flipped to an opposite side of the knee joint while still pinned if desired to make additional or even third or more access portals or tracks as shown in FIG. 5. This feature makes the procedure to create additional entry points remarkably easy. Once the two access portals 12, 14 are created, the use of a visualizing camera system 70 as the surgeon uses other devices and instruments to remove or repair the lesion 10 is available so real time observation of the surgical repair is available which vastly improves the likelihood of successful lesion tissue removal and treatment. Once the lesion 10 cavity is cleared, substances 62 can be added through the access portal. One such substance 62 is bone cement that can greatly improve screw or pin fixation.

Essentially the next aspect of this is taking bone marrow lesions 10 with ocd and osteochondritis dissecans and when the surgeon is trying to fix these, generally the bone 7 behind it is poor so he is not getting very good fixation so the two additional elements are needed after one utilizes the technique, either after or during utilization of the technique the surgeon can actually put screws in place, they can be metal or they can be biocomposite. These fixation devices 90 actually go into the lesion 10 then he can put the substance 62 around it, the grout or a bone cement which may include different types of bone cement, different types of putty 62, which might harden when set actually allow the screw to be better fixed, alternatively he can put the bone cement substance 62 in the lesion cavity first, then screw directly through it which can again both of these provide better fixation than without any of the bone substances 62. The cement is either put around once the screws are placed or the screws 90 are placed through it. And these can be screws or these can be darts or any variety of fixation devices 90.

FIG. 8 is the picture showing what an OCD lesion would look like intra articular, you can see the cartilage wrap 5 coming off and the subchondral bone 7 behind it. Often you can't see the bone behind it. This one is a lesion 10 that is more advanced and fixation pins 90 are placed to stabilize the bone.

FIG. 9 is a picture with 3 photos 9A, 9B and 9C above it showing how a lesion 10 has completely come off and that is what the bone 7 looks behind it. There is more dead bone behind that we want to access so either you could have a cartilage cap that was intact on it or you have the exposed bone. That is why with the guide system 20 one can go through either cartilage 5 or intact bone 7 when it is exposed. That bone is called subchondral bone 7. Again, the surgeon wants to get behind it and he can't see it, that's why he wants to pass the tip or end of the pinning member and that's the tip end that he wants to access blindly from a different portal 12, 14. One can see on FIG. 9 that's the x-ray which shows what a lesion 10 like this might look like, and one can try to pin that lesion or try to get behind it.

The FIG. 8 illustration of this is an actual photograph just shows how one currently can secure that lesion 10, stabilize with screws or degradable pins 90, 92. The present invention technique is more predicated upon actually a couple of different things. Number one addressing the tissue behind that bone and then more importantly, once that has been actually addressed that tissue, where bone marrow lesion has been removed can be filled with substances such as cement, etc. Now the surgeon can fix into those substances which is another extension of this system because one of the things now that can be done because one has created an appropriate bed behind that lesion you now have new techniques of fixation which can actually fix into that bone which currently cannot be done because there is no way of stressing that foundation absent this type of repair.

The second or the first entry access itself or the track created can be enlarged. It's important to note that the second entry access, although generally extra-articular, does not necessarily have to be so. More importantly, this access track can be away from the cartilage and subchondral bone so that it does not damage these structures. The current state of the art does not allow for addressing lesions of bone distant to the entry point of the localizing site. It is also important to restate that the present inventive technique allows for accessing or accessing as well as addressing the lesion. Specifically, although the surgeon can address bone lesions by removing damaged tissue, sometimes he can choose to address them by simply adding structural materials or stem cells or both without removing any tissue.

An important feature of this technique is that fixation of the lesion utilizing stabilizing devices such as the initial localizing pin or additional ones which can now either be drilled or punched through the lesion and then be filled with the grout material, such as concrete being poured on rebar, or filling with the grout material before and then the fixation device is placed through it, such as placing screws through concrete once it has set. This introduces an entirely new methodology of addressing these lesions which previously has not been effectively or precisely performed.

With reference to FIGS. 10-12, a normal joint with a lesion 10 is shown where the lesion has been prepared forming a cavity in the region 10 and 10A. In this cavity, bone anchors, screws, or anchors or pins 90 can be positioned as illustrated in FIG. 10. These pins and screws 90 enter into the cavity location as shown in FIG. 10. With reference to FIG. 11, when a syringe 60 is positioned into the entry access 12, the syringe filled with bone cement 62 can be used to deliver bone cement or other adhesive or bonding material into the cavity 10 or 10A of the lesion 10. When this occurs, the bone cement 62 encapsulates and surrounds the anchors 90 that have previously been positioned as illustrated in FIG. 10. As the cement fills the cavity, the syringe 60 can be backed out and as illustrated in FIG. 10, the entire entry access portal 12 can be filled. This provides a secure structurally enhanced repair of the area where the lesion 10 or abnormality had existed, as illustrated in FIG. 12. Alternatively, a bone repair mixture 62 can be inserted into the cavity via the entry access portal 12 and then the screws or pins 90 can be positioned drilling into the cement 62. If the cement 62 is soft, it will simply go into the cavity and will surround the screws or pins 90 with the cement 62 which will harden later or alternatively if provided with sufficient cutting flutes, can be threaded into the prepared area with the cement 62 already hardened. Any of these methodologies are possible with the benefit that the damaged knee will be strengthened substantially by the introduction of the bone hardening cement 62 into the cavity 10, 10A via the entry access 12.

Figure 14:
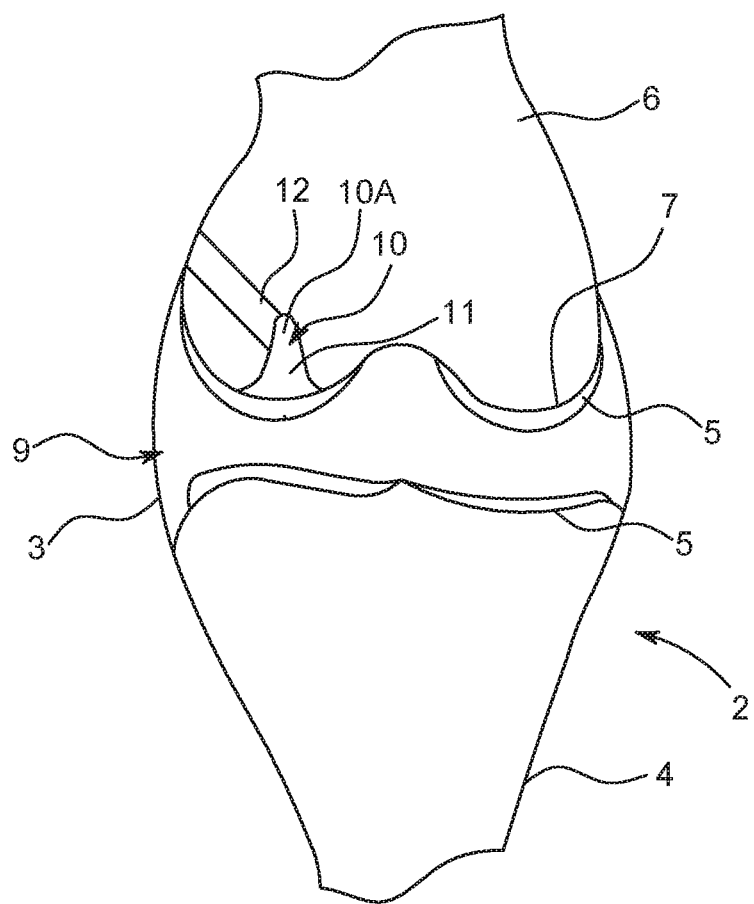
FIG. 14 shows the created second entry access to the lesion without a physical access through the subchondral bone or cartilage when performing the method of the second embodiment.
Figure 15:
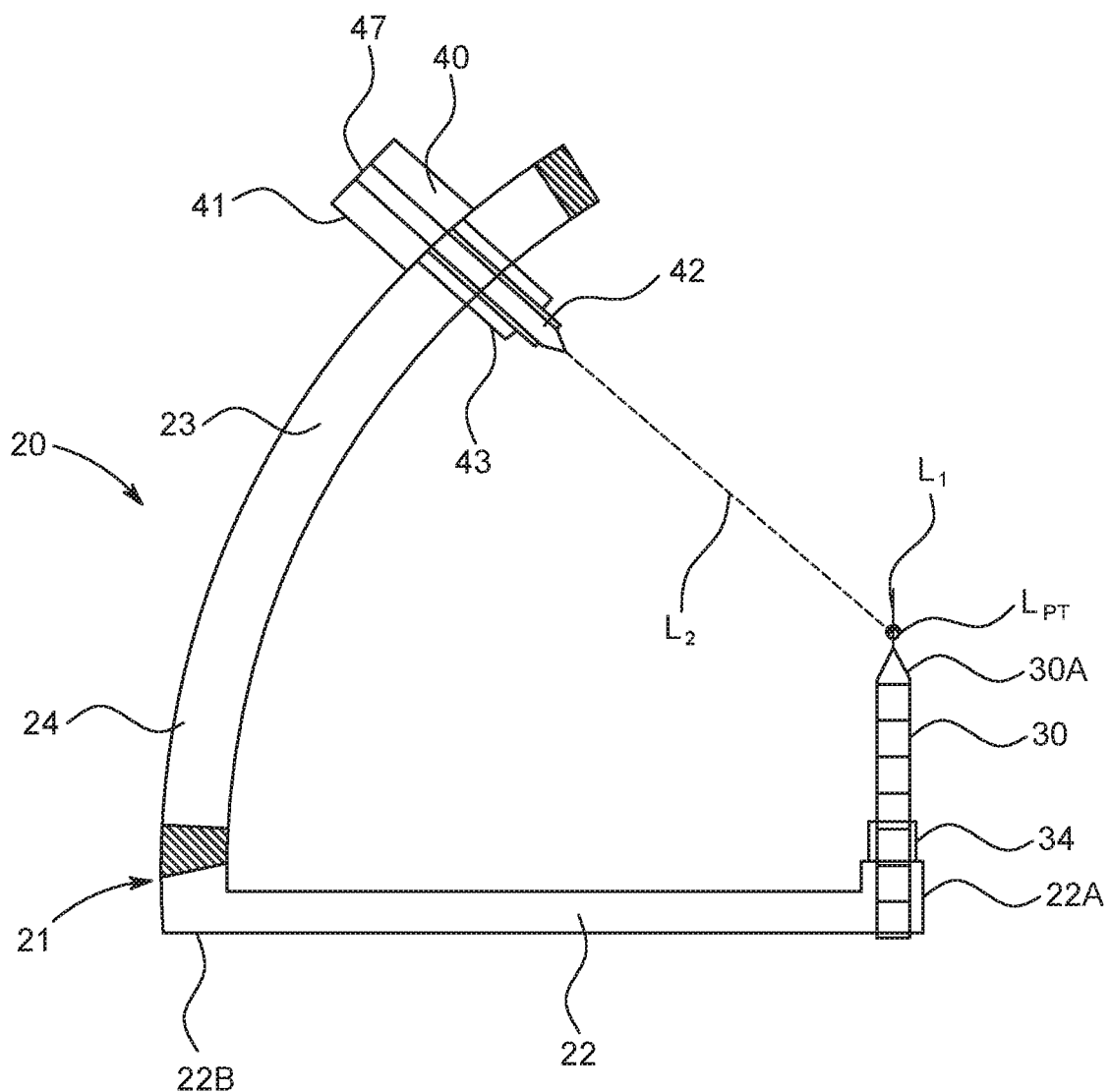
FIG. 15 is a plan view of the guide system of the second embodiment.
Figure 16:
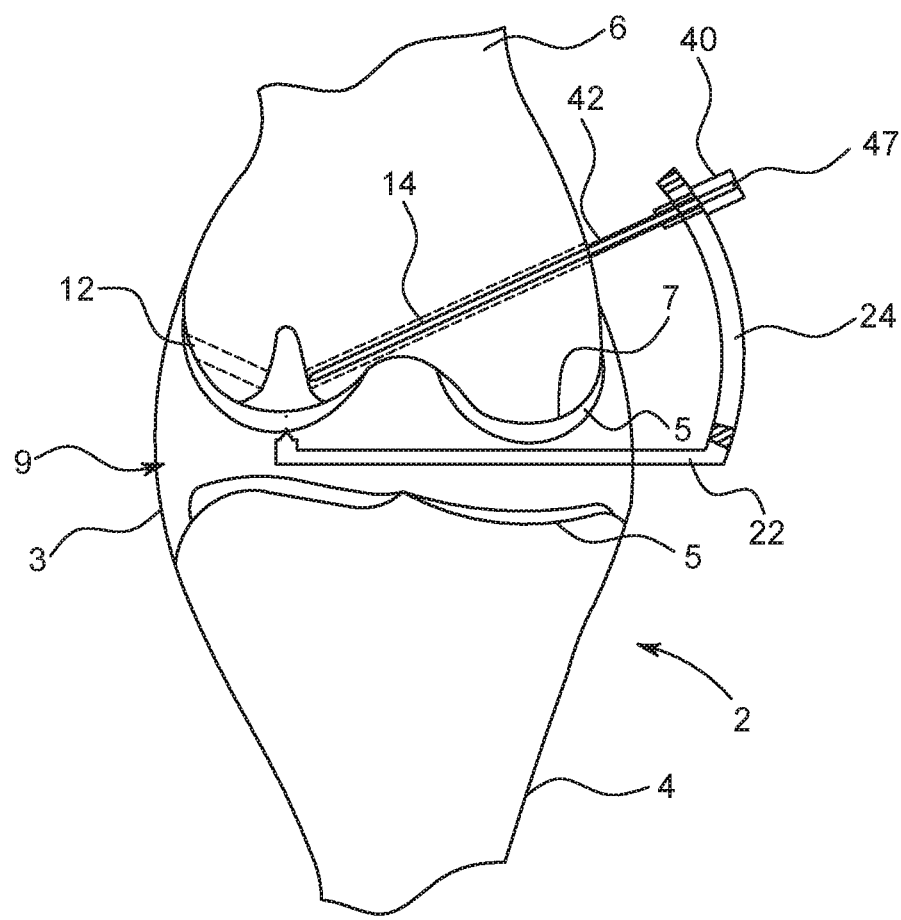
FIG. 16 is a second view of the joint of FIG. 15 showing an additional entry access with the guide system of the second embodiment in place.
Figure 17:
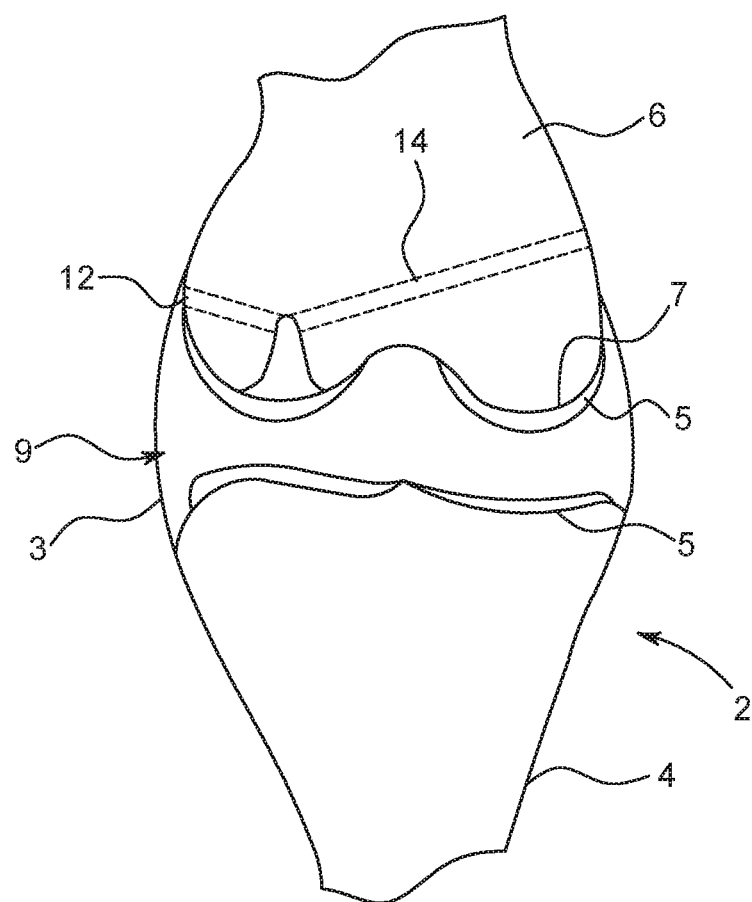
FIG. 17 shows the second view with the guide system of the second embodiment removed.
Figure 18:
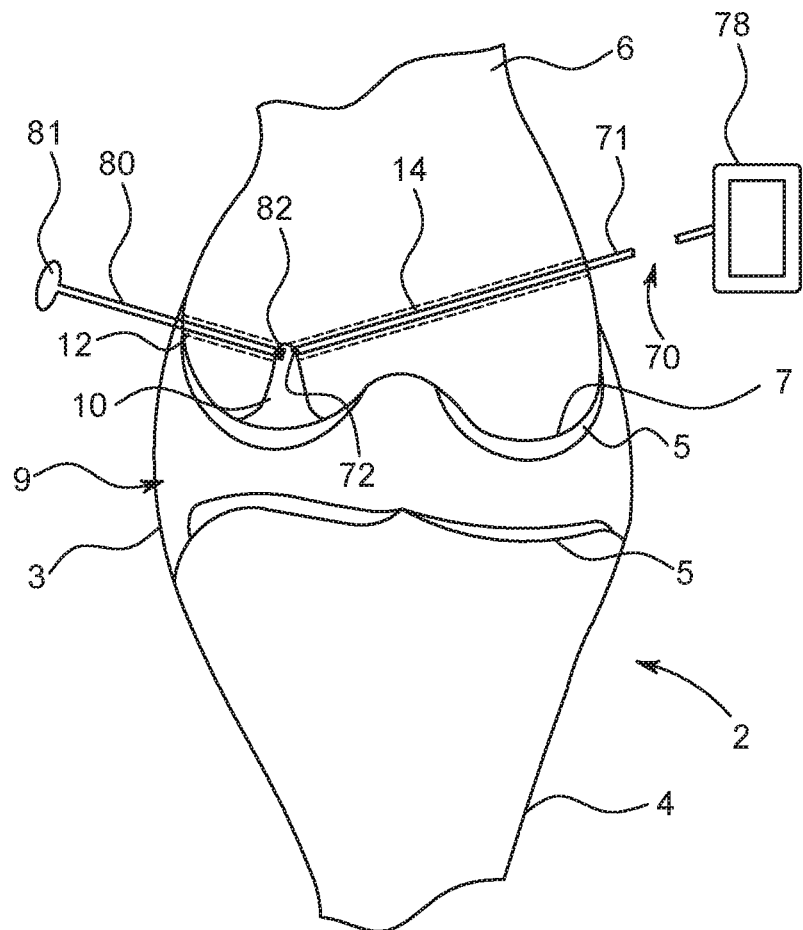
FIG. 18 shows a camera in the second entry access.

With reference to FIGS. 13-18, a second embodiment of the invention is shown. The second embodiment uses a guide component 21 similar to the guide component 21 of the first embodiment. However, in this embodiment, the localizing pinning member 30 is short, shown truncated, having a point or tip 30A that can rest onto the cartilage 5 above the subchondral bone 7. In this location 11A, the tip 30A can be pinned onto the cartilage 5 so that it is held there by the surgeon and the entry access portal 12 can be created using the movable guide 40. The movable guide 40 can then have a drill, punch or trocar 50 directed into the bone towards the lesion 10 to create an entry access portal 12. As illustrated in FIG. 14, the entry access portal 12 is shown approaching the region of the lesion 10 and is delivered to a desired target location within the lesion. What is unique about the second embodiment method is, as shown in FIG. 14, there is no hole or first entry access tunnel 11 created by the localizing pinning member 30 instead a virtual pathway 11V is created by the guide component 21. As shown in FIG. 15, the guide component 21 has the arcuate arm 24 with the movable guide 40 that can be positioned anywhere along the angular approach of the arcuate arm portion 24. The straight arm portion 22 holds the localized pinning member 30. The localized pinning member 30 may have gradations 33 as previously discussed along the shank of the pinning member 30. However, the pinning member 30 has an end 30A that rests on top of the cartilage 5 and subchondral bone 7 such that a virtual pathway 11V along line $L_1$ is created pointing into the lesion 10. If desired, when the movable guide 40 is positioned along the arcuate arm portion 24, a second line $L_2$ is created. The intersection of lines $L_1$ and $L_2$ creates the desired target location or point $L_{PT}$ as illustrated. The benefit of this component is that no cartilage or subchondral bone needs to be cut or drilled into using this device. As shown in FIG. 16, the entry access portal 14 is already created using the virtual pathway 11V that was further described with reference to FIG. 13. In FIG. 16, however, the device can be then pivoted in such a fashion that an additional access portal 14 can be created on an opposite side of the joint as illustrated. Again, when pivoting the guide 21, the subchondral bone and cartilage are never penetrated through, however, all access portals will be directed along the virtual pathway 11V of the localized pinning member 30. With reference to FIG. 17, multiple entry access portals 12 and 14 are illustrated. With reference to FIG. 18, a device 80, 81 is shown on one side with the device 70 with a camera viewing the area of the lesion 10 through the additional access portal 14. In this fashion, the device 80 can be used to probe into the cavity where the surgeon observes what is happening using the camera 70.

Figure 19:
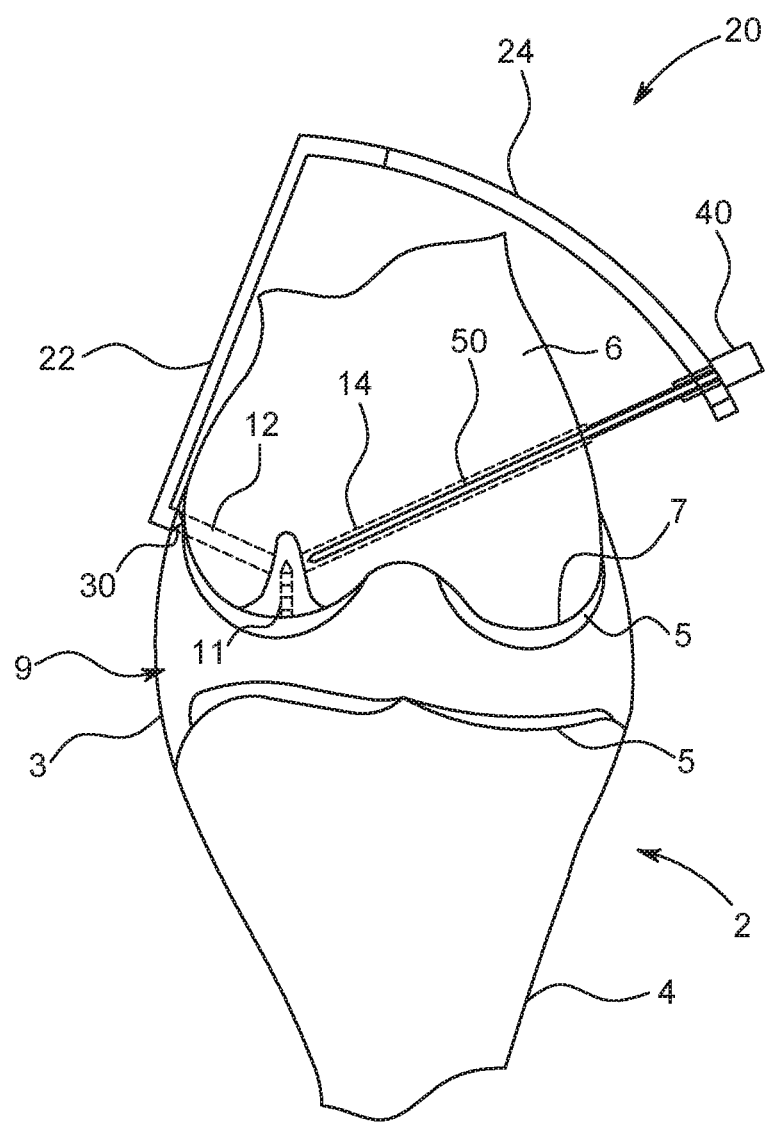
FIG. 19 is a use of either guide component wherein the localizing pining member is moved to the second access entry to create additional access entry.

With reference to FIG. 19, the guide component 21 can be repositioned such that the localized pinning member 30 is positioned in the entry access 12. When this occurs, the surgeon can locate an additional location for an entry access or an additional entry access 14 by simply pivoting the guide component 21 about the localized pinning member 30 positioned in the access portal 12 in such a fashion that the movable guide 40 can then be positioned and directed such that an additional entry access portal 14 can be drilled on the opposite side of the bone. In the embodiment of FIG. 19, a pin 90 is shown positioned in the area of the lesion 10. This method of moving the localized pinning member 30 to an entry access portal for making additional entry access portals can be used with either the first embodiment of the invention or the second embodiment of the invention.

Figure 20:
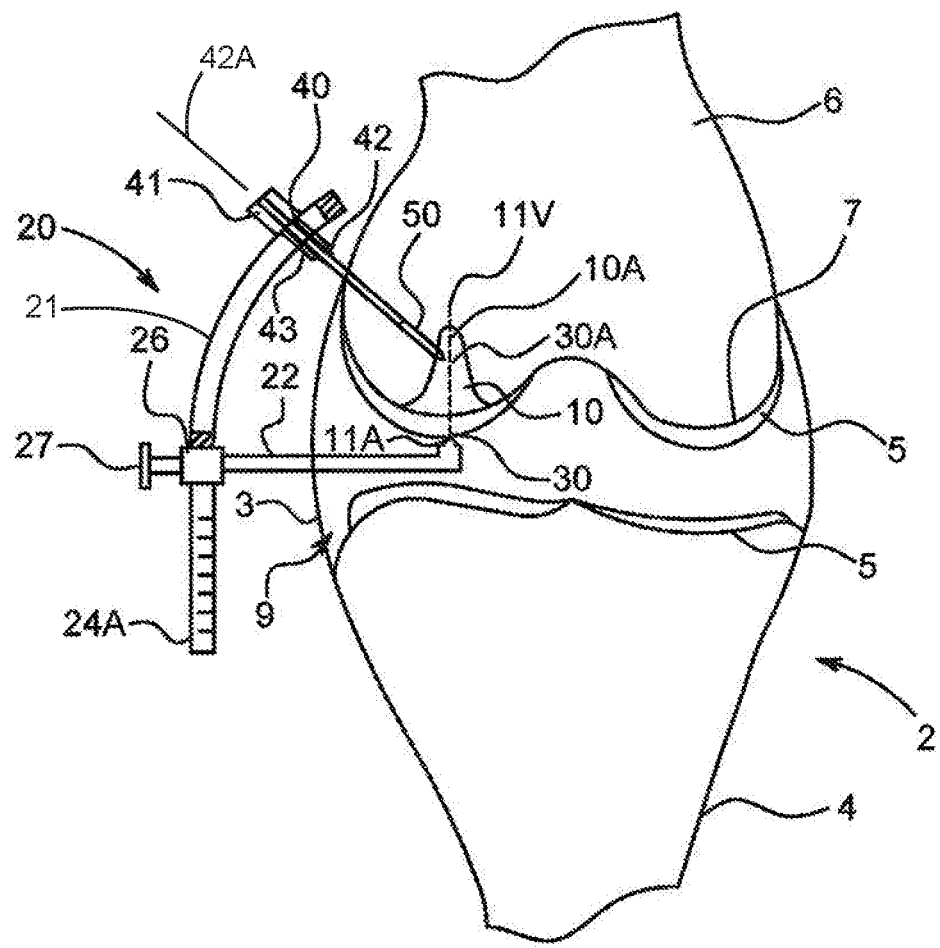
FIG. 20 demonstrates the guide system of the third embodiment of the invention wherein the guide component second arm is adjustably movable relative to the first arm, as shown the first arm has a virtual localizing pin of the second embodiment.
Figure 20A:
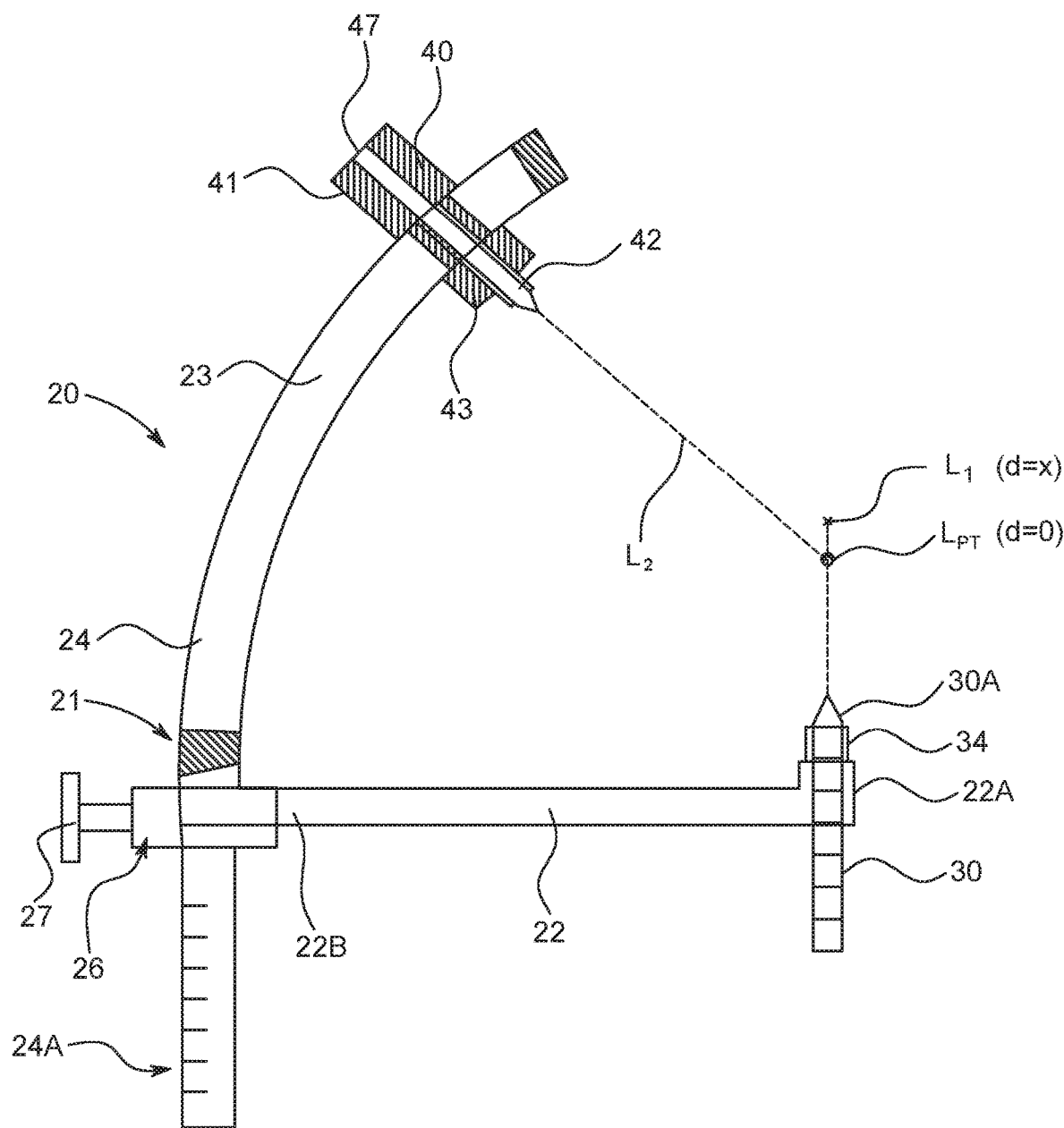
FIG. 20A demonstrates an alternative version of the third embodiment wherein the first arm has an adjustable localizing pion member of the first embodiment.
Figure 20B:
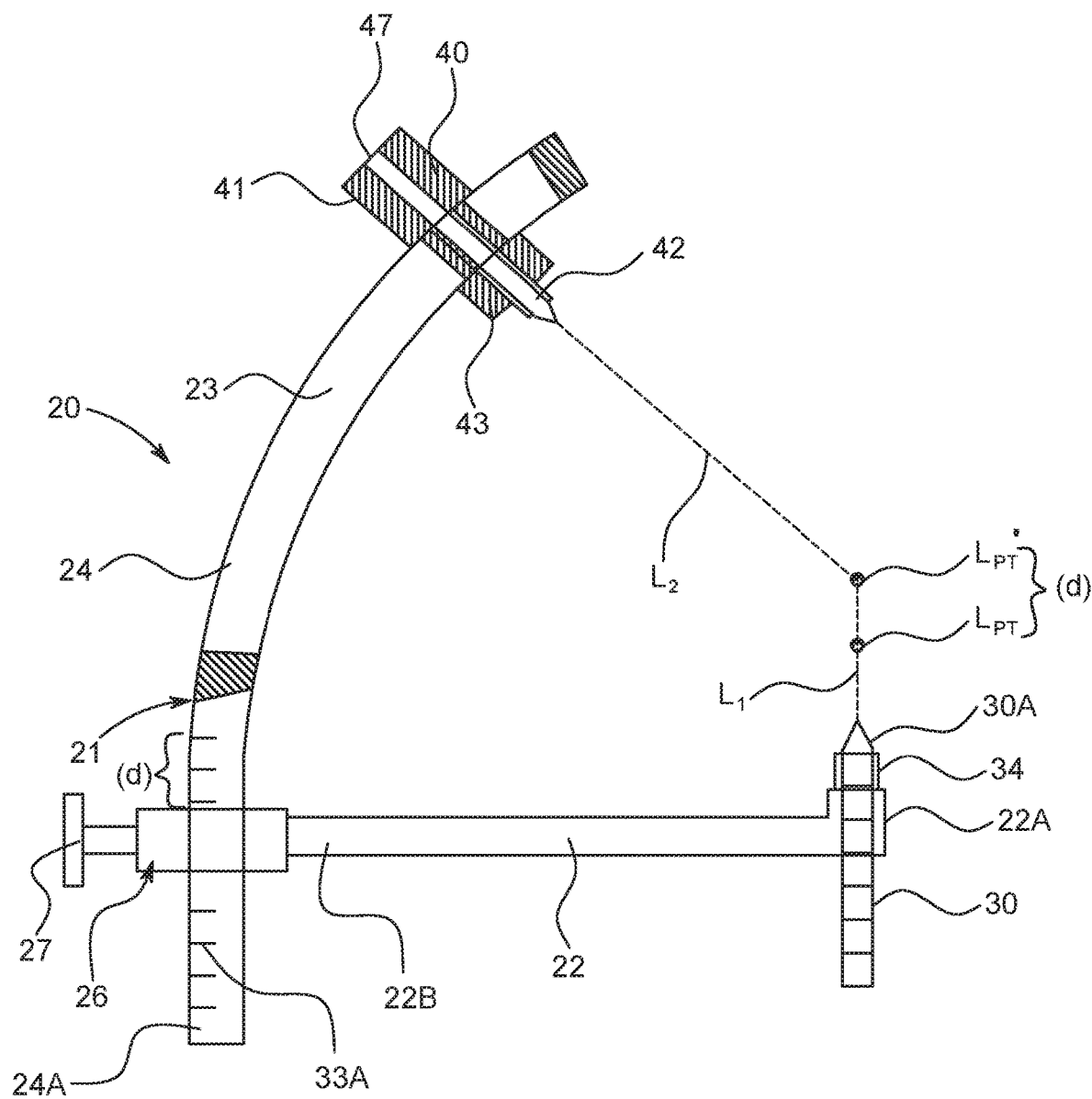
FIG. 20B shows the guide system of the third embodiment wherein the second arm is shown moved a selected distance (d) relative to the first arm wherein this adjustment moves the intersect location Lpt by the selected distance (d) thereby shift the first entry access parallel to the initial setting per-translated to allow a redirected shifted Lpt intersect.
Figure 21:
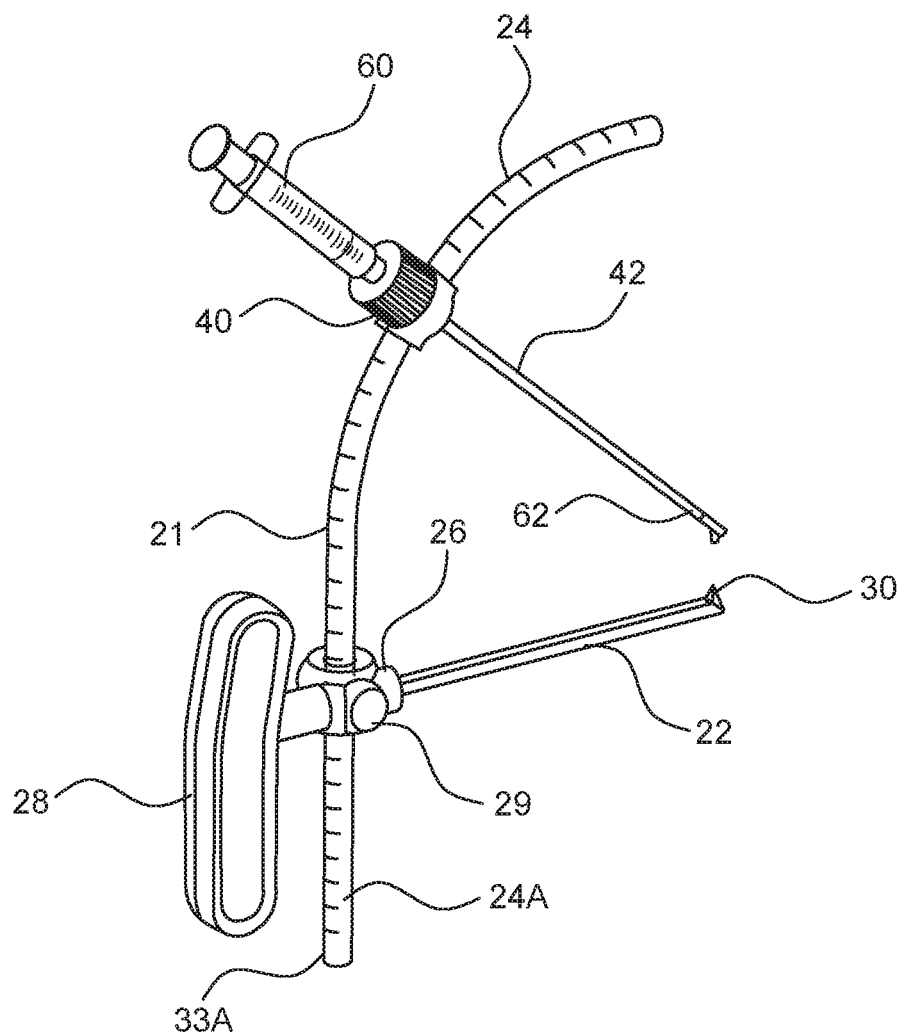
FIG. 21 is a perspective view of the third embodiment with an alternative guide component showing a syringe positioned to fill a prepared lesion.
Figure 22:
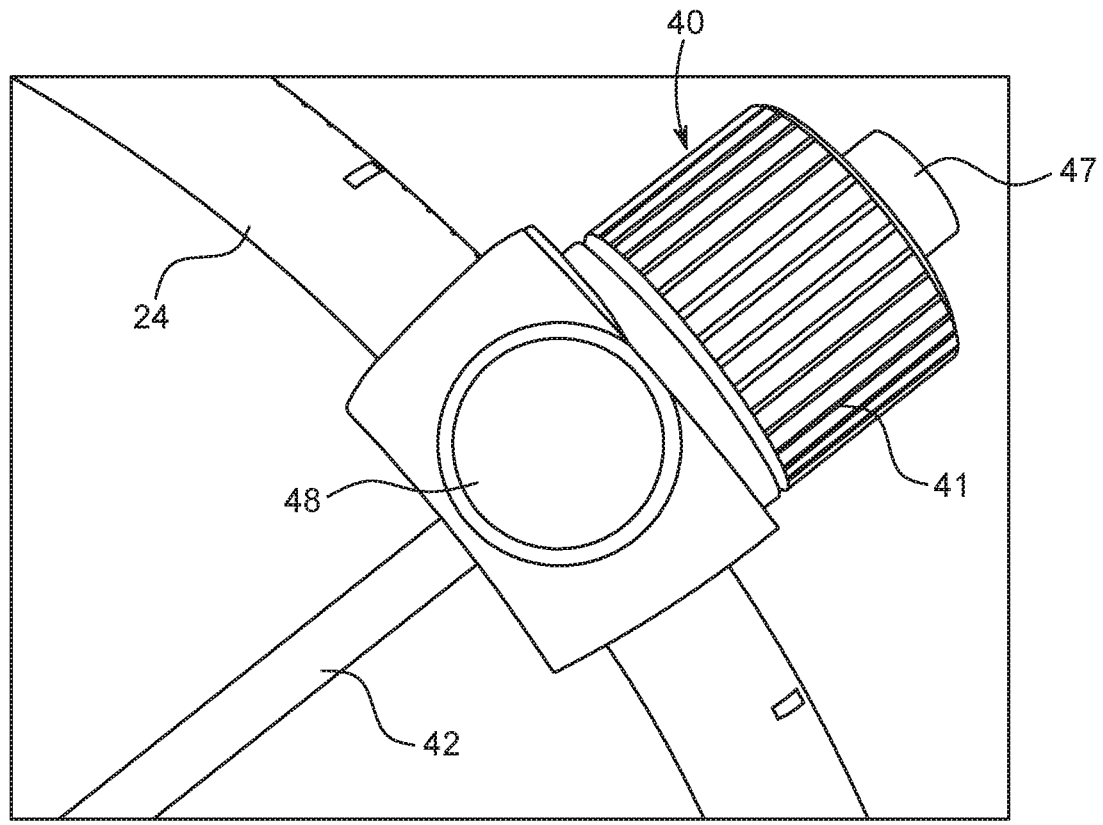
FIG. 22 is an enlarged view of the movable guide of the third embodiment.
Figure 23:
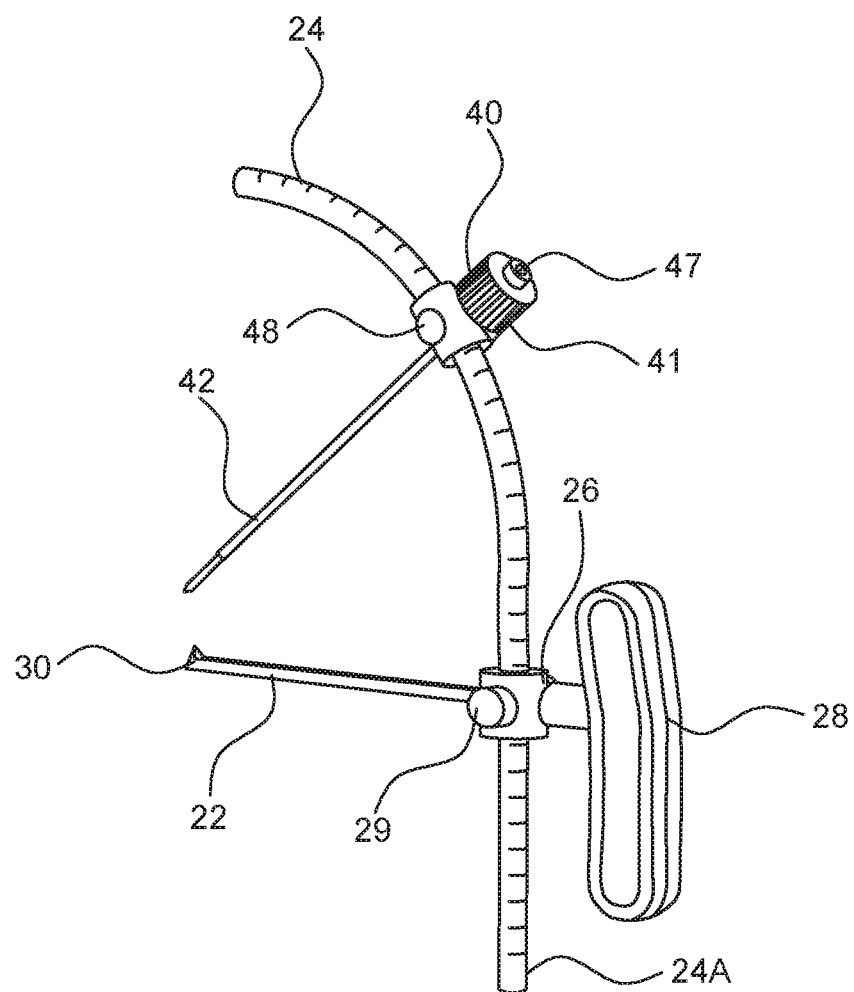
FIG. 23 is a second perspective view taken from FIG. 21 without the syringe.
Figure 24:
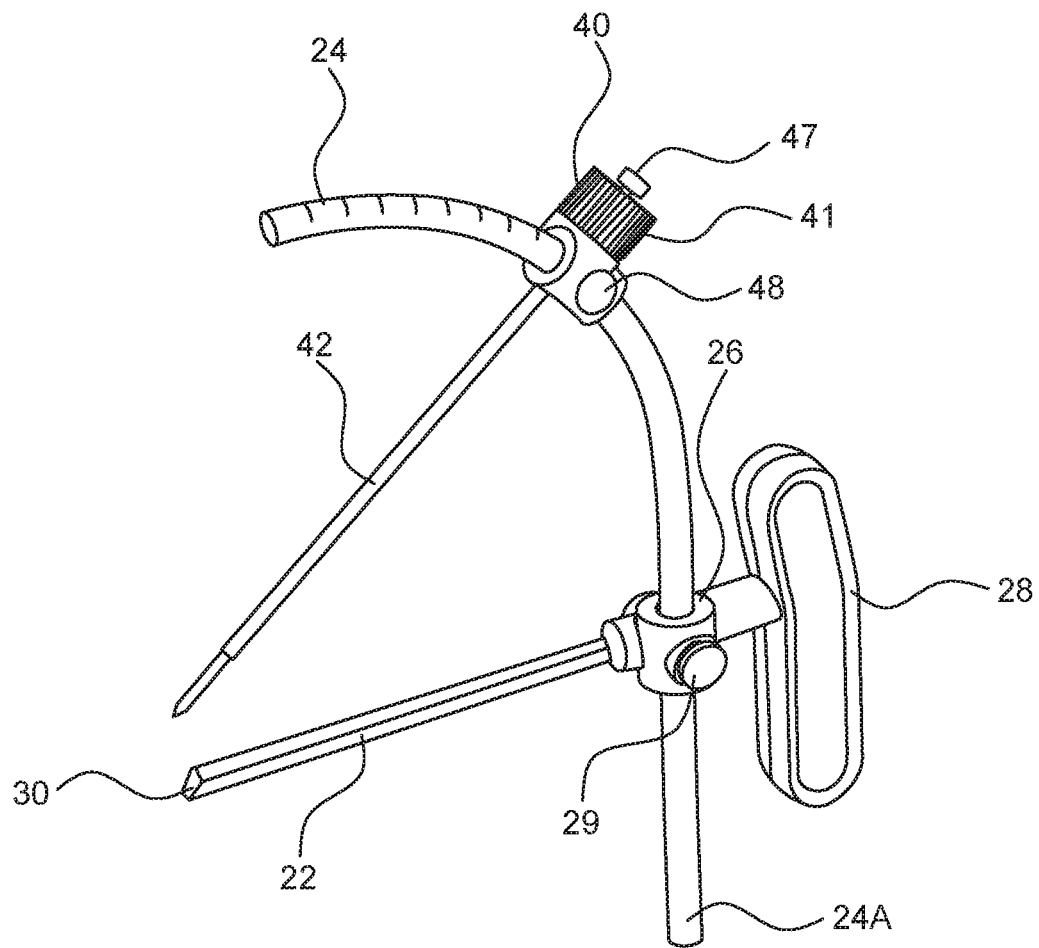
FIG. 24 is another perspective view of the third embodiment.
Figure 25:
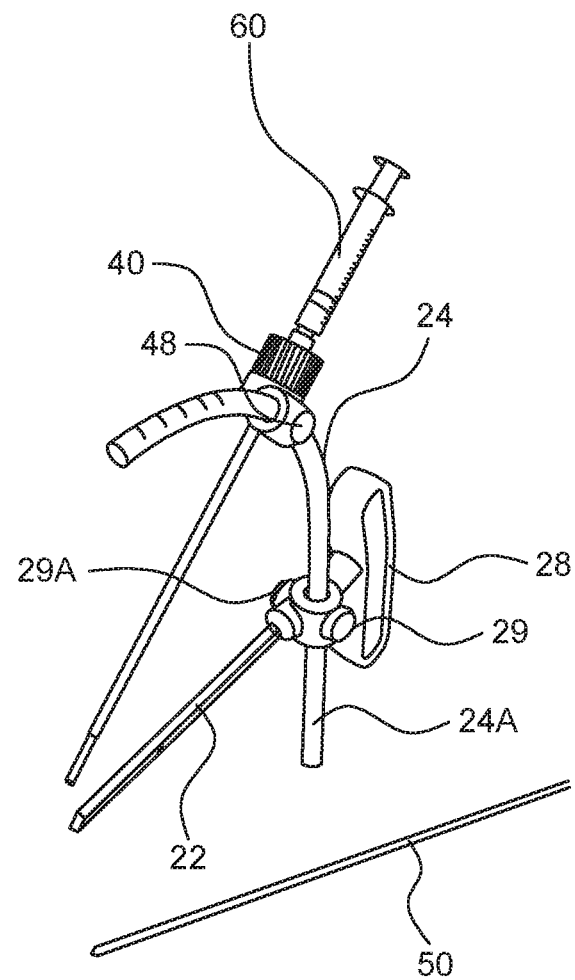
FIG. 25 shows a syringe for passing material through a cannulated sleeve in the entry access, a drill is shown in the fore view.
Figure 26:
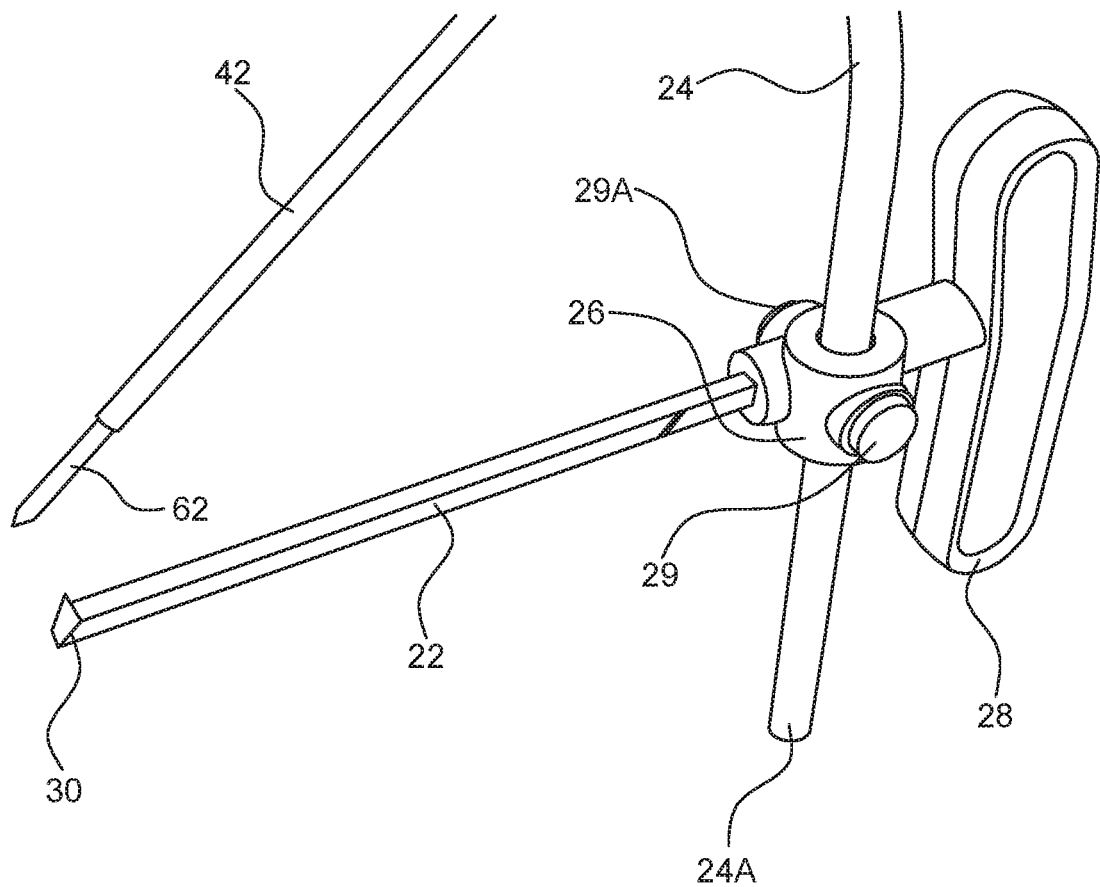
FIG. 26 shows a portion of the third embodiment guide system and the drill extending through the guide sleeve.

With reference to FIGS. 20-27, the present invention is shown with a third embodiment having a guide component that is suitable for use with the virtual pathway concept of the second embodiment as shown in FIGS. 20, 21, 26 or the localizing pinning member 30 of the first embodiment as illustrated in FIGS. 20A and 20B. The guide component 21 has the first arm 22 for holding the localizing pinning member 30 detachable from the device. The first arm 22 is coupled to a coupling end 26. The coupling end 26 is configured to move along a straight portion 24A of the second arm 24. The straight portion 24A extends to the curved arcuate portion of the second arm 24. As illustrated in FIGS. 20, 20A and 20B the second arm 24 is shown having a slot 23 that allows the movable guide 40 to slide in the slot 23 over a range of angles. As in previous embodiments, the second arm 24 is shown in a partial section view showing a slot 23 that allows a movable guide 40 to slide in the slot 23 over a range of angles between at least 0 and 90 degrees relative to the tip of the pinning member 30, most typically between 30 and 60 degrees. Preferably, the movable guide 40 has a cannulated shaft, sleeve or tube 42 with a tightening clamp 41 having a nut 43 that fixes the movable guide 40 onto the second arm 24 anywhere along the slotted opening or slot 23. The cannulated shaft, sleeve or tube 42 defines an axis 42A extending longitudinally therethrough, wherein the axis 42A intersects virtual pathway 11V. As shown, a drill bit, a punch or a trocar 50 can be slipped through the movable guide 40 tube 42 to create the second access portal or track 12, 14. Preferably, when locating the desired location to form the second or additional access portals, the tube 42 is moved relative to the guide 21 to set the tube solidly against the tissue then the components are tightened to fix the angle and the sleeve length. Then the drill 50 can be inserted to create the second or more access tracks or portals 12, 14. The shape of the guide component 21 allows the system 20 to be pinned at one location and flipped to an opposite side of the knee joint while still pinned if desired to make additional or even third or more access portals or tracks as shown in FIG. 5. This feature makes the procedure to create additional entry points remarkably easy. Once the two access portals 12, 14 are created, the use of a visualizing camera system 70 as the surgeon uses other devices and instruments to remove or repair the lesion 10 is available so real time observation of the surgical repair is available which vastly improves the likelihood of successful lesion tissue removal and treatment. Once the lesion 10 cavity is cleared, substances 62 can be added through the access portal. One such substance 62 is bone cement that can greatly improve screw or pin fixation.

What is clearly different from the first two embodiments is the straight portion 24A provides a way for the surgeon to precisely adjust the track of the drill forming an entry access 14 without changing the angle established by the movable guide component 40. This is achieved by moving the second arm 24 relative to the first arm 22 from an initial position from d=0 to a shifted position by a second distance d=x by moving the coupling end 26 of the first arm 22 along the straight portion 24A by precisely having the second arm 24 moved relative to the coupling 26 and of the first arm 22. This shift by a preselected distance (x) correspondingly shifts the track of the entry access exactly a distance (x). This means the surgeon can move the entry track without altering the angle. The secondary adjustment enables the surgeon to select an optimal access to the region in or near the lesion or abnormality that is being treated. It is not uncommon for the optimal entry approach angle to provide a track that is not exactly ideal for a treatment. This added feature of adjusting an entry track by a precise offset distance allows the angulation to remain optimally fixed as the location is shifted by a pre-selected offset distance (d). This results in the initial entry access track is shifted to an offset track that is parallel to the original initial access track as the shift adjustment being clearly shown in FIGS. 20A and 20B. In FIG. 20A, the initial track $L_2$, shown in dashed lines, intersects line L at $L_{PT}$ and when the second arm 24 is shifted a distance (d) relative to the coupling 26 and locked in by a thumb screw 27, the access track line $L_2$ is shifted to $L_{PT}'$ the same distance (d). This capability to adjust angulation at the arcuate portion 24 and also shift to an offset distance at the straight portion 24A affords the surgeon a convenient and very reliable way to create blind access openings for treating lesions and other abnormalities. This includes the treatment of tumors and infections in addition to the other problems discussed. Specifically, with respect to tumors, the surgeon can introduce stabilizing materials such as different types of bone substitutes as well as cement. It also allows him to deliver targeted ablation agents and chemotherapy. With respect to bone infections, it can also allow for delivery of bone agents and cement as well as antibiotics. These are both incredible indications that heretofore were never really accessible so precisely being nearly impossible to target indications.

A variation of the system for accessing extra articular lesions or abnormalities of the third embodiment is illustrated in FIGS. 21-26. In this variation, the guide component 21 is made in a simplified structure where the second arm 24 is made as a solid rod having a straight portion 24A and an arcuate portion 24 formed as a single piece without a slot. As shown, the movable coupling 26 and the movable guide 40 are simply slipped onto the guide component 21. The calibrated gradations 33A are shown extending all along the guide component 21 in both the straight portion 24A and the arcuate portion 24. The movable guide 40 has a sleeve 42 detachably connected and the guide 40 has a locking button 48 which, when depressed, allows movement of the guide 40 about the arcuate arm 24 and, when released, holds the guide 40 in a fixed position. The locking feature 48 can be constructed in a variety of alternatives such as a thumb screw or its equivalent. Similarly, the coupling 26 has a similar locking button 29 that when depressed releases so the second arm 24 along the straight portion 24A can be adjusted as previously discussed. As shown, the device of this embodiment has a handle 28 to provide the surgeon a convenient way to hold the system 20 as he sets his access track and his offset to precisely pinpoint the track of an entry access. As noted, the device can be moved to create multiple entry access openings if so desired. At the end of the movable guide 40 is an access portal 47 provided to receive a syringe 60 or camera 72 or any other tool that may be needed to pass into an entry access opening formed by a drill 50 or punch or tap, shown in FIG. 25.

As shown in FIG. 26, the drill 50 or punch or tap is guided through the sleeve 42 when set to create an access opening. One important aspect of the system is an axis of the localized pinning member 30 and an axis of the guide sleeve 42 in every embodiment shown lie in a single plane. This insures the virtual pathway $L_1$ and the access track $L_2$ when extended will intersect. The surgeon, when creating the entry access opening, can select the depth of the opening to be created short of the point of intersection, at the point of intersection or past and beyond it. This can be done by simply drilling to a predetermined distance, the surgeon can mark on the drill 50 and when that mark is reached, he can know exactly where an end of the access opening is, which in this invention can be called the desired target location.

Figure 27:
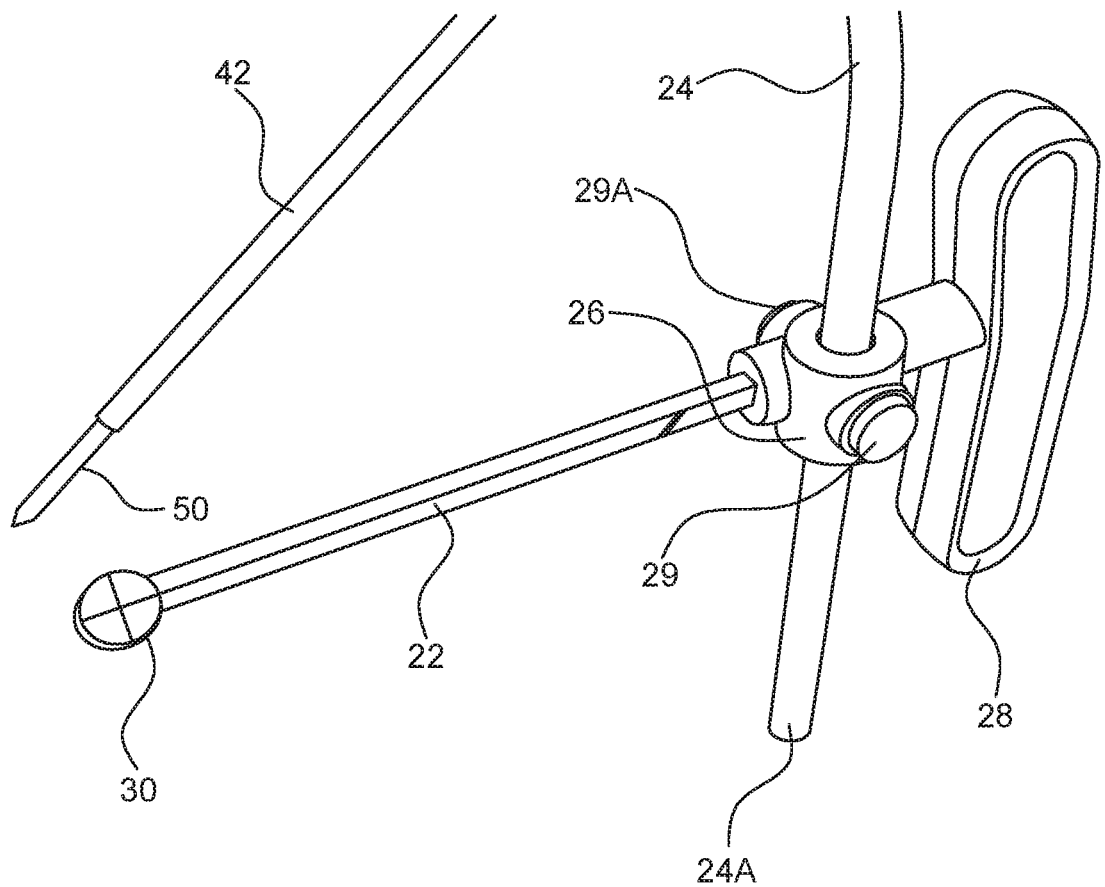
FIG. 27 shows a virtual localizing pin configured as a flat oval tip with a centered target cross-hair feature.

The system 20 shows the localizing pinning member 30 as a pointed elongated pin 30, or a short virtual pin 30. As shown in FIG. 27, the pin 30 can be made as an oval or annular ring at the end of the first arm 22. The annular ring preferably has a cross-hair centered in the opening creating a virtual target observable by the surgeon. Alternatively, the pinning member 30 can be cannulated to form an access entry sleeve if so desired.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating a compromised portion of a bone structure, comprising:
    providing a virtual pathway access apparatus comprising an instrument guide body, an offset distance adjustor engaged with a straight portion of the instrument guide body to move along said straight portion and an angular orientation adjuster engaged with an arcuate portion of the instrument guide body to move along said arcuate portion, wherein the offset distance adjustor has a localizing pinning member integral therewith at a location laterally spaced away from a longitudinal axis of the straight portion of the instrument guide body, wherein a longitudinal axis of the localizing pinning member defines a virtual pathway extending colinear therewith above a tip of the localizing pinning member and parallel with the longitudinal axis of the straight portion of the instrument guide body and wherein a central passage of the angular orientation adjuster defines an access axis extending colinear with a longitudinal axis of the central passage;
    determining a reference location on an exterior surface of the bone structure and a target location within the compromised portion of the bone structure, wherein a distance therebetween defines an offset distance;
    jointly setting the offset distance adjustor and the angular orientation adjuster at respective positions on the instrument guide body such that a distance between the tip of the localizing pinning member and a point at which the access axis intersects the virtual pathway is approximately the same as the offset distance, wherein the access axis extends through the bone structure at a location remote from the reference location and intersects the target location;
    engaging the tip of the localizing pinning member with the exterior surface of bone structure at the reference location;
    orienting the virtual pathway access apparatus such that the virtual pathway and the access axis both extend through the target location while the tip of the localizing pinning member is engaged with the reference location of the bone structure; and
    forming, at least partially to the target location, an access passage along the access axis through the bone structure using an access instrument engaged with an access instrument mounting structure integral with the angular orientation adjuster while the tip of the localizing pinning member is engaged with the exterior surface of bone structure at the reference location, wherein the orientation of the virtual pathway access apparatus, the offset distance and the respective positions of the offset distance adjustor and the angular orientation adjuster on the instrument guide body jointly define a point of entry of the access passage into the bone structure that is remote from the reference location.

2. The method of claim 1, wherein said orienting of the virtual pathway access apparatus includes manipulating the orientation of the virtual pathway reference apparatus while maintaining the tip of the localizing pinning member in engagement with the reference location of the bone structure.

3. The method of claim 1, wherein
    the access instrument being engaged with the access instrument mounting structure mechanically constrains an angular orientation of the access instrument relative to the virtual pathway and the access axis.

4. The method of claim 1, further comprising:
    forming, along the access axis through the bone structure using the access instrument engaged with the access instrument mounting structure at least partially to the target location, an additional access passage at a location spaced away from the access passage after forming the access passage;
    wherein forming the additional access passage includes rotating, while maintaining the tip of the localizing pinning member in contact with the exterior surface of the bone structure at the reference location, the virtual pathway access apparatus about the virtual pathway from an angular position at which the access passage is formed to a different position at which the additional access passage is to be formed.

5. The method of claim 4, further comprising:
    visualizing at least a portion of the target location through a first one of said access passages; and
    surgically altering the compromised portion of the bone structure through a second one of said access passages while performing said visualizing.

6. The method of claim 4, wherein said orienting of the virtual pathway access apparatus includes manipulating the orientation of the virtual pathway reference apparatus while maintaining the tip of the localizing pinning member in engagement with the reference location of the bone structure.

* * * * *